United States Patent [19]

Malabarba et al.

[11] Patent Number: 5,521,155
[45] Date of Patent: May 28, 1996

[54] AMIDES OF TEICOPLANIN COMPOUNDS

[75] Inventors: Adriano Malabarba, Binasco; Giorgio Tarzia, Saronno, both of Italy

[73] Assignee: Gruppo Lepetit S.p.A, Gerenzano, Italy

[21] Appl. No.: 389,425

[22] Filed: Feb. 14, 1995

Related U.S. Application Data

[62] Division of Ser. No. 221,661, Mar. 31, 1994, abandoned, which is a continuation of Ser. No. 79,970, Jun. 17, 1993, abandoned, which is a continuation of Ser. No. 884,324, May 11, 1992, abandoned, which is a continuation of Ser. No. 581,446, Sep. 11, 1990, abandoned, which is a continuation of Ser. No. 405,086, Sep. 6, 1989, abandoned, which is a continuation of Ser. No. 224,181, Jul. 22, 1988, abandoned, which is a continuation of Ser. No. 906,701, Sep. 11, 1986, abandoned.

[30] Foreign Application Priority Data

Sep. 12, 1985 [GB] United Kingdom .................. 8522574

[51] Int. Cl.[6] .......................... A61K 38/12; A61K 38/14; C07K 9/00; C07K 7/54
[52] U.S. Cl. .................. 514/8; 514/9; 530/317; 530/322; 530/323
[58] Field of Search .................................. 530/317, 322, 530/323; 514/8, 9

[56] References Cited

U.S. PATENT DOCUMENTS

| | | | |
|---|---|---|---|
| 3,981,303 | 9/1976 | Higuchi et al. | 424/428 |
| 4,239,751 | 12/1980 | Coronelli et al. | 424/118 |
| 4,497,802 | 2/1985 | Debono | 530/322 |
| 4,534,969 | 8/1985 | Phillips | 424/118 |
| 4,604,239 | 8/1986 | Michel et al. | 530/317 |
| 4,629,781 | 12/1986 | Strazzolini et al. | 530/317 |
| 4,645,827 | 2/1987 | Malabarba et al. | 530/322 |
| 4,650,855 | 3/1987 | Malabarba et al. | 530/322 |
| 4,698,418 | 10/1987 | Malabarba et al. | 530/317 |
| 5,198,418 | 3/1993 | Malabarba | 514/8 |

FOREIGN PATENT DOCUMENTS 0301785  2/1989  European Pat. Off. .

OTHER PUBLICATIONS

March, Advanced Organic Chemistry, 2nd Edition, McGraw–Hill Kogakusha, Ltd. Tokyo, pp. 382–389 and 1276–1277 (1977).

Primary Examiner—Christina Y. Chan
Attorney, Agent, or Firm—J. Michael Dixon

[57] ABSTRACT

The present invention is directed to an amide derivative of the glycopeptide, teicoplanin. This compound is an antibiotic that is active against gram positive bacteria. This compound is produced by subjecting teicoplanin to an amidation reaction.

3 Claims, No Drawings

AMIDES OF TEICOPLANIN COMPOUNDS

This is a division of application Ser. No. 08/221,661, filed Mar. 31, 1994, now abandoned, which is a continuation of application Ser. No. 08/079,970, filed Jun. 17, 1993, now abandoned, which is a continuation of application Ser. No. 07/884,324, filed May 11, 1992, now abandoned, which is a continuation of application Ser. No. 07/581,446, filed Sep. 11, 1990, now abandoned, which is a continuation of 07/405,086, filed Sep. 6, 1989, now abandoned, which is a continuation of application Ser. No. 07/224,181, filed Jul. 22, 1988, now abandoned, which is a continuation of application Ser. No. 06/906,701, filed Sep. 11, 1986, now abandoned, which is herein incorporated by reference.

The present invention is directed to amides of teicoplanin compounds having the following formula I:

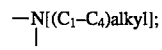
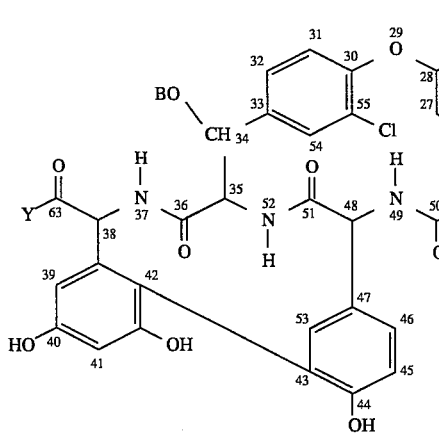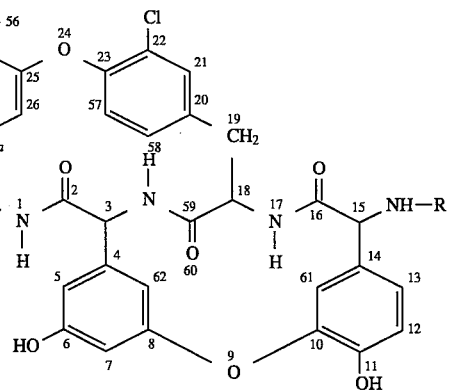

wherein

R represents hydrogen or a protecting group of the amine function

Y represents a group

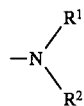

wherein

R$^1$ represents hydrogen, ($C_1$–$C_6$) alkyl, hydroxy ($C_2$–$C_4$) alkyl, halogeno($C_2$–$C_4$)alkyl, ($C_1$–$C_4$)alkoxy($C_2$–$C_4$)alkyl, amino($C_2$–$C_4$)alkyl, ($C_1$–$C_4$)alkylamino($C_2$–$C_4$)alkyl, di($C_1$–$C_4$)alkylamino($C_2$–$C_4$) alkyl R$^2$ represents hydrogen, ($C_1$–$C_6$) alkyl, hydroxy ($C_2$–$C_4$) alkyl, halogeno($C_2$–$C_4$)alkyl, ($C_1$–$C_4$)alkoxy($C_2$–$C_4$)alkyl, a nitrogen containing 5–6 membered heterocyclic ring which may be unsaturated, partially saturated or wholly saturated and may contain 1 to 3 further heteroatoms selected from N, S and O wherein 1 to 3 of the ring carbons may optionally bear ($C_1$–$C_4$)alkyl substituents and one of the ring nitrogens may optionally bear a substituent R$^5$ selected from ($C_1$–$C_4$) alkyl, ($C_4$–$C_7$)cycloalkyl, phenyl optionally substituted with halogen or ($C_1$–$C_4$) alkyl, phenyl ($C_1$–$C_4$) alkyl, pyridyl, ($C_1$–$C_4$)alkylpyridinio, and when the ring is wholly saturated two of the ring members may optionally be bridged by an alkylene chain of 1 to 3 carbon atoms wherein one of the methylene groups may optionally be replaced by —NH— or —N[($C_1$–$C_4$)alkyl];

a group -alk-W wherein "alk" represents a linear alkylene chain of 1 to 8 carbon atoms which is optionally substituted with a substituent selected from ($C_1$–$C_4$)alkyl, hydroxy ($C_1$–$C_4$) alkyl, hydroxy, carboxy, aminocarbonyl, ($C_1$–$C_4$)alkylaminocarbonyl, di($C_1$–$C_4$)alkylaminocarbonyl, ($C_1$–$C_4$)alkoxycarbonyl, phenyl ($C_1$–$C_4$)alkoxycarbonyl, and W represents a carboxy, ($C_1$–$C_4$)alkoxycarbonyl, phenyl($C_1$–$C_4$)alkoxycarbonyl, aminocarbonyl, ($C_1$–$C_4$) alkylaminocarbonyl, di($C_1$–$C_4$)alkylaminocarbonyl pentosaminocarbonyl, hexosaminocarbonyl, ureido, guanidino, a nitrogen containing 5–6 membered heterocyclic ring defined as above, a group of the formula

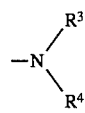

wherein R$^3$ and R$^4$ each independently represent hydrogen, ($C_1$–$C_6$)alkyl, hydroxy($C_2$–$C_4$)alkyl and halogeno($C_2$–$C_4$)alkyl, or R$^4$ represents phenylmethyloxycarbonyl and R$^3$ represents hydrogen; a group of the formula

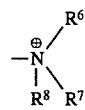

wherein R$^6$ R$^7$ and R$^8$ each independently represent a ($C_1$–$C_4$) alkyl, or R$^1$ and R$^2$ taken together with the adjacent nitrogen atom represent a saturated 5–7 membered heterocyclic ring which may optionally bear one to two ($C_1$–$C_4$)alkyl substituents on the ring carbons and may contain a further heterogroup selected from —O—, —S—, and —NR$^5$— wherein R$^5$ is defined as above;

A represents hydrogen or —N[($C_{10}$–$C_{11}$)aliphatic acyl]-β-D-2-deoxy-2-amino-glucopyranosyl, B represents hydrogen or N-acetyl-β-D-2-deoxy-2-amino-glucopyranosyl, M represents hydrogen or α-D-mannopyranosyl;

with the proviso that B represents hydrogen only when A and M are simultaneously hydrogen and M represents hydrogen only when A is hydrogen and with the further proviso that when W represents a group

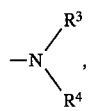

a group

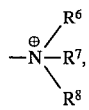

ureido, guanidino or a nitrogen containing 5–6 membered heterocyclic ring as defined above directly connected with the "alk" moiety through a bond with a ring nitrogen atom, the linear alkylene "alk" moiety must be of at least two carbon atoms;

and the addition salts thereof.

Teicoplanin is the international non-proprietary name (INN) of the antibiotic substance formerly named teichomycin which is obtained by cultivating the strain *Actinoplanes teichomyceticus* nov. sp. ATCC 31121 in a culture medium containing assimilable sources of carbon, nitrogen and inorganic salts (see U.S. Pat. No. 4,239,751). According to the procedure described in the above cited patent an antibiotic complex containing Teichomycin $A_1$, $A_2$ and $A_3$ is recovered from the separated fermentation broth by extraction with a suitable water insoluble organic solvent and precipitation from the extracting solvent according to common procedures. Teichomycin $A_2$, which is the major factor of the isolated antibiotic complex, is then separated from the other factors by means of column chromatography on SEPHADEX. British Patent Application Publication No. 2121401 discloses that antibiotic Teichomycin $A_2$ actually is a mixture of five closely related co-produced main components. *Actinoplanes teichomyceticus* ATCC 31121 was deposited under the terms of the Budapest Treaty. This deposit occurred on Jan. 30, 1975 and was accepted under the terms of the Budapest Treaty on Jan. 31, 1981. This depository was the American Type Culture Collection (ATCC) whose address is 12301 Parklawn Drive, Rockville, Md. 20852. According to recent structural studies it is possible to represent teicoplanin $A_2$ (formerly Teichomycin $A_2$) main components 1, 2, 3, 4 and 5 by the above formula I wherein R is hydrogen, Y is hydroxy, A represents —N[($C_{10}$–$C_{11}$)aliphatic acyl]-β-2-deoxy-2-amino-glucopyranosyl, B represent N-acetyl-β-D-2-deoxy-2-amino-glucopyranosyl, M represents α-D-manno-pyranosyl.

More particularly, in teicoplanin $A_2$ component 1, the [($C_{10}$–$C_{11}$)-aliphatic acyl] substituent represents Z-decenoyl, in teicoplanin $A_2$ component 2 represents 8-methylnonanoyl, in teicoplanin $A_2$ component 3 represents decanoyl, in teicoplanin $A_2$ component 4 represents 8-methyldecanoyl, in teicoplanin $A_2$ component 5 represents 9-methyldecanoyl.

All the sugar moieties, when present, are linked to the teicoplanin nucleus through O-glycosidic bonds.

In addition, it has been found that it is possible to transform teicoplanin, a pure factor thereof or a mixture of any of said factors in any proportion, into unitary antibiotic products by means of selective hydrolysis of one or two sugar moieties. They are named antibiotic L 17054 and antibiotic L 17046 and are described in European Patent Application Publication No. 119575 and European Patent Application Publication No. 119574, respectively. Preferred hydrolysis conditions for the production of antibiotic L 17054 are: 0.5N hydrochloric acid at a temperature between 70° C. and 90° C. and for a time which is generally between 15 and 90 min. Antibiotic L 17054 is represented by the above formula I wherein Y is hydroxy, R and A represent hydrogen, B represents N-acetyl-β-D-2-deoxy-2-amino-glucopyranosyl, M represents α-D-mannopyranosyl wherein the sugar moieties are linked to the peptidic nucleus through an O-glycosidic bond.

Preferred hydrolysis conditions for the preparation of antibiotic L 17046 are: 1–3N hydrochloric acid, at a temperature between 50° and 90° C. and for a time which is generally between 30 and 60 min.

Antibiotic L 17046 is represented by the above formula I wherein Y is hydroxy, R, A and M represent hydrogen atoms, and B is N-acetyl-β-D-2-deoxy-2-amino-glucopyranosyl wherein the sugar moiety is linked to the peptidic nucleus through an O-glycosidic bond.

The complete selective cleavage of all the sugar moieties of the teicoplanin compounds gives an aglycone molecule which is called antibiotic L 17392, or deglucoteicoplanin, and is represented by the above formula I wherein Y is hydroxy, and R, A, B, and M each individually represents a hydrogen group. This selective hydrolysis process is described in European patent application No. 84114558.4.

A substance having the same structural formula is disclosed in European Patent Application Publication No. 0090578 and is named antibiotic A 41030 factor B. This substance is obtained by means of a microbiological process which involves the fermentation of the strain *Streptomyces virginiae* NRRL 12525 or *Streptomyces virginiae* NRRL 15156 in a suitable medium, the isolation, purification and separation into its components of antibiotic A 41030, an antibiotic complex of at least seven factors, antibiotic A 41030 factor B, included.

All the above named compounds, i.e. teicoplanin, teicoplanin $A_2$ complex, teicoplanin $A_2$ component 1, teicoplanin $A_2$ component 2, teicoplanin $A_2$ component 3, teicoplanin $A_2$ component 4, teicoplanin $A_2$ component 5, antibiotic L 17054, antibiotic L 17046, antibiotic L 17392 and any mixture thereof in any proportion, are suitable starting materials for the preparation of the amide derivatives of the invention. In the present specification "teicoplanin compound" or "teicoplanin starting material" is used to indicate any one of the above starting materials, i.e. teicoplanin as obtained according to U.S. Pat. No. 4,239,751, any further purification thereof, teicoplanin $A_2$ complex, a compound of the above formula I wherein R is hydrogen, Y is hydroxy, A represents hydrogen or —N[($C_{10}$–$C_{11}$)aliphatic acyl]-β-D-2-deoxy-2-amino-glucopyranosyl, B represent hydrogen or N-acetyl-β-D-2-deoxy-2-amino-glucopyranosyl, M represents hydrogen or α-D-mannopyranosyl, with the proviso that B may represent hydrogen only when A and M are simultaneously hydrogen and M may represent hydrogen only when A is hydrogen, a salt thereof, or a mixture thereof in any proportion.

As used herein the term "alkyl", either alone or in combination with other substituents, includes both straight and branched hydrocarbon groups; more particularly, "($C_1$–$C_6$)alkyl" represents a straight or branched aliphatic hydrocarbon chain of 1 to 6 carbon atoms such as methyl, ethyl, propyl, 1-methylethyl, butyl, 1-methylpropyl, 1,1-dimethylethyl, pentyl, 1-methylbutyl, 2-methylbutyl, 1-hexyl, 2-hexyl, 3-hexyl, 3,3-dimethyl-1-butyl, 4-methyl-1-pentyl, and 3-methyl-1-pentyl likewise, "($C_1$–$C_4$)alkyl" represents a straight or branched hydrocarbon chain of 1 to 4 carbon atoms such as those alkyl of 1 to 4 carbons exemplified above. The term "halogeno" represents an halogen atom selected from fluorine, chlorine, bromine and iodine. The pentosamino moieties of the pentosaminocarbonyl substituent are 2- or 3-amino (2- or 3-deoxy) either D or L or D, L pentose group in either anomeric form or in an anomeric mixture, such as 2- or 3-amino(2- or 3- deoxy)-ribose, 2- or 3-amino(2- or 3-deoxy)arabinose, 2- or 3-amino(2- or 3-deoxy)xylose and 2- or 3-amino (2 or 3-deoxy)lyxose. The hexosamino moieties of the hexosaminocarbonyl substituent are either D or L, or (D, L) 2- or 3-amino (2- or 3-deoxy)hexose group in either anomeric form or in an anomeric mixture such as 2- or 3-amino(2- or 3-deoxy)allose, 2- or 3-amino(2- or 3-deoxy)altrose, 2- or 3-amino(2- or 3-deoxy)glucose, 2- or 3-amino(2- or 3-deoxy)mannose, 2- or 3-amino (2- or 3-deoxy)gulose, 2- or 3-amino (2- or 3-deoxy)galactose, and 3- or 4-amino(2- or 3-deoxy) fruttofuranose.

"Linear alkylene chains of 1 to 8 carbon atoms" as defined in the present application are straight alkylene chains of 1, 2, 3, 4, 5, 6, 7 or 8 carbon atoms. Representative examples of linear alkylene chains of 1 to 8 carbon atoms are:
—CH$_2$—
—CH$_2$—CH$_2$—
—CH$_2$—CH$_2$—CH$_2$—
—CH$_2$—CH$_2$—CH$_2$—CH$_2$—
—CH$_2$—CH$_2$—CH$_2$—CH$_2$—CH$_2$—
—CH$_2$—CH$_2$—CH$_2$—CH$_2$—CH$_2$—CH$_2$—
—CH$_2$—CH$_2$—CH$_2$—CH$_2$—CH$_2$—CH$_2$—CH$_2$—
—CH$_2$—CH$_2$—CH$_2$—CH$_2$—CH$_2$—CH$_2$—CH$_2$—CH$_2$—

These linear alkylene chains optionally may bear substituents as described above. The expression "a nitrogen containing 5–6 membered heterocyclic ring which may contain 1 to 3 further heteroatoms selected from N, S and O" according to the present invention includes unsaturated, partially saturated and wholly saturated ring systems such as pyridinyl, pyrimidinyl, pyrazinyl, pyrrolidinyl, piperidinyl, piperazinyl, oxazolyl, oxazolinyl, oxazolidinyl, pyrazolinyl, pyrazolidinyl, thiazolidinyl, morpholinyl, thiomorpholinyl, pyrrolyl, pyrrolinyl, imidazolyl, imidazolidinyl, thiadiazolyl, oxadiazolyl, and tetrazolyl. In said "nitrogen containing 5–6 membered heterocyclic ring" 1 to 3 ring carbons may optionally bear (C$_1$–C$_4$)alkyl substituents defined as above. When a ring carbon is saturated, it may be simultaneously substituted with two (C$_1$–C$_4$)alkyl groups. When the above defined "nitrogen containing 5–6 membered heterocyclic ring" is a wholly saturated ring, this definition includes also those heterocyclic rings which have two ring members bridged by an alkylene chain of 1 to 3 carbon atoms wherein a methylene group may optionally be replaced by a group —NH— or

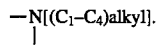

Examples of said bridged rings are the following:
1-azabicyclo[2.2.2]octane, 1,4-diazabicyclo[3.2.2]nonane, 1-azabicyclo[2.2.1]heptane, 1-azabicyclo[3.2.1]octane, 8-azabicyclo[3.2.1]octane, 3-azabicyclo[3.2.1]octane, 1-azabicyclo[3.3.1]nonane, 9-azabicyclo[3.3.1]nonane, 3,8-diazabicyclo[3.2.1]octane, 2-azabicyclo[2.2.1]heptane, 2-azabicyclo[2.2.2]octane, 3-azabicyclo[3.2.2]nonane.

Accordingly, representative compounds of this invention include those of the general formula above where the symbol

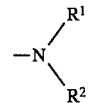

represents a substituent derived from one of the following moieties:
1-azabicyclo[2.2.2]octan-3-amine, 1-azabicyclo[2.2.2]octan-2-amine, 1-azabicyclo[2.2.2]octan-3-amine, 6-methyl 1-azabicyclo[2.2.2]octan-3-amine, N-methyl 1-azabicyclo[2.2.2]octan-3-amine, 1-azabicyclo[2.2.2]octan-3-ethanamine, 1-azabicyclo[2.2.2]octan-4-amine, 1-azabicyclo[2.2.2]octan-4-amine, N-methyl 1-azabicyclo[2.2.2]octan-2-methanamine, 1-azabicyclo[2.2.1]heptan-3-amine 8-azabicyclo[3.2.1]octan-3-methanamine, 8-azabicyclo[3.2.1]octan-3-amine, 8-methyl 8-azabicyclo[3.2.1]octan-3-amine, 8-ethyl 3-azabicyclo[3.2.1]octan-2-methanamine, 1-azabicyclo[3.2.1]octan-3-ethanamine, 1-azabicyclo[3.3.1]nonan-4-amine 1-azabicyclo[3.3.1]nonan-3-methanamine 9-azabicyclo[3.3.1]nonan-3-amine, 9-methyl 2-azabicyclo[2.2.1]heptan-5-amine, 2-methyl 2-azabicyclo[2.2.2]octan-5-amine, 2-methyl The expression "a saturated 5–7 membered heterocyclic ring which may optionally bear one to two (C$_1$–C$_4$)alkyl substituents on the ring carbons and may optionally contain a further heterogroup selected from —O—, —S— and —NR$^5$—" include, for instance, the following heterocyclic groups: morpholinyl, piperidinyl, piperazinyl, thiomorpholinyl, pyrazolidinyl, 1,3-oxazolidinyl, 1,3-thiazolidinyl and hexahydroazepinyl, which may optionally be substituted by one or two (C$_1$–C$_4$)alkyl group on the carbon skeleton.

A preferred group of compounds of the invention is represented by those compounds of formula I wherein R represents a hydrogen atom and the other substituents are as defined above. A further preferred group of compounds of the invention are those compounds of formula I wherein R and R$^1$ represent hydrogen and the other substituents are as above defined. A further preferred group of compounds of the invention is represented by those compounds of formula I wherein R represents hydrogen Y represents a group

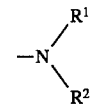

wherein

R represents hydrogen, (C$_1$–C$_6$) alkyl,

R$^2$ represents (C$_1$–C$_6$)alkyl, a nitrogen containing 5–6 membered heterocyclic ring which may be unsaturated, partially saturated or wholly saturated and may contain 1 to 3 further heteroatoms selected from N, S and O wherein 1 to 3 of the ring carbons may optionally bear (C$_1$–C$_4$)alkyl substituents and one of the ring nitrogens may optionally bear a substituent R$^5$ selected from (C$_1$–C$_4$)alkyl, (C$_4$–C$_7$)cycloalkyl, phenyl, and pyridyl;

a wholly saturated nitrogen containing 5–6 membered heterocyclic ring which may contain a further N atom wherein 1 to 3 of the ring carbons may optionally bear (C$_1$–C$_4$)alkyl substituents, one of the ring nitrogens may optionally bear a substituent R$^5$ representing (C$_1$–C$_4$)alkyl and two of the ring members are bridged by an alkylene chain of 1 to 3 carbon atoms wherein one of the methylene groups may optionally be replaced by —NH— or

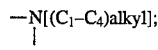

a group -alk-W wherein "alk" represents a linear alkylene chain of 1 to 8 carbon atoms which is optionally substituted with a substituent selected from $(C_1-C_4)$alkyl, carboxy, aminocarbonyl, $(C_1-C_4)$ alkylaminocarbonyl, di$(C_1-C_4)$ alkylaminocarbonyl, $(C_1-C_4)$ alkoxycarbonyl, phenyl$(C_1-C_4)$alkoxycarbonyl, and W represents a carboxy, $(C_1-C_4)$alkoxycarbonyl, phenyl$(C_1-C_4)$alkoxycarbonyl, aminocarbonyl, $(C_1-C_4)$alkylaminocarbonyl, di$(C_1-C_4)$alkylaminocarbonyl glucosaminocarbonyl, ureido, guanidino, a nitrogen containing 5–6 membered heterocyclic ring which may be unsaturated, partially saturated or wholly saturated and may contain 1 to 3 further heteroatoms selected from N, S and O wherein 1 to 3 of the ring carbons may optionally bear $(C_1-C_4)$alkyl substituents and one of the ring nitrogens may optionally bear a substituent $R^5$ selected from $(C_1-C_4)$alkyl, $(C_4-C_7)$cycloalkyl, phenyl, and pyridyl; a wholly saturated nitrogen containing 5–6 membered heterocyclic ring which may contain a further N atom wherein 1 to 3 of the ring carbons may optionally bear $(C_1-C_4)$alkyl substituents, one of the ring nitrogens may optionally bear a substituent $R^5$ representing $(C_1-C_4)$alkyl and two of the ring members are bridged by an alkylene chain of 1 to 3 carbon atoms wherein one of the methylene groups may optionally be replaced by —NH— or

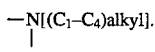

a group of the formula

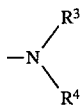

wherein $R^3$ and $R^4$ each independently represent hydrogen, $(C_1-C_6)$alkyl, hydroxy$(C_2-C_4)$alkyl and halogeno$(C_2-C_4)$alkyl, or $R^4$ represents phenylmethyloxycarbonyl and $R^3$ represents hydrogen; a group of the formula

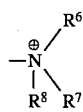

wherein $R^6$ $R^7$ and $R^8$ each independently represent a $(C_1-C_4)$alkyl, or $R^1$ and $R^2$ taken together with the adjacent nitrogen atom represent a saturated 5–7 membered heterocyclic ring which may optionally bear one to two $(C_1-C_4)$alkyl substituents on the ring carbons and may contain a further heterogroup selected from —O—, —S—, and —NR$^5$— wherein $R^5$ is defined as above;

A represents hydrogen or N-{$C_{10}$-$C_{11}$aliphatic acyl}-β-D-2-deoxy-2-amino-glucopyranosyl, B represents hydrogen or N-acetyl-β-D-2-deoxy-2-amino-glucopyranosyl, M represents hydrogen or α-D-mannopyranosyl;

with the proviso that B represents hydrogen only when A and M are simultaneously hydrogen and M represents hydrogen only when A is hydrogen and with the further proviso that when W represents a group

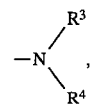

a group

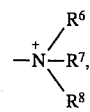

ureido, guanidino or a nitrogen containing 5–6 membered heterocyclic ring as defined above directly connected with the "alk" moiety through a bond with a ring nitrogen atom, the linear alkylene "alk" moiety must be of at least two carbon atoms;

and the addition salts thereof.

A further preferred group of compounds of the invention includes those compounds of formula I wherein R and $R^1$ represent hydrogen and $R^2$ represents a group -alk-W wherein "alk" is a linear alkylene chain of 2 to 8 carbon atoms, W represent pyrrolidino, morpholino, thiomorpholino, piperidino or a piperazino optionally substituted on the N'nitrogen atom with a $(C_1-C_6)$alkyl, $(C_4-C_7)$cycloalkyl, benzyl, pyridinyl, or $(C_1-C_4)$alkylpyridinio group or W represents a group of the formula

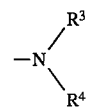

wherein $R^3$ and $R^4$ each independently represent a $(C_1-C_6)$alkyl group and A, B and M are the same as above and the acid addition salts thereof. Also preferred compounds of the invention are represented by those compounds of formula I wherein R, $R^1$, A, B and M represent hydrogen atoms and $R^2$ represents a group

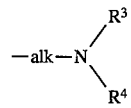

wherein "alk" is a linear alkylene chain of 2 to 6 carbon atoms and $R^3$ and $R^4$ represent $(C_1-C_6)$alkyl groups and the pharmaceutically acceptable addition salts thereof.

Another group of preferred compounds of the invention are those compounds of formula I wherein R represents hydrogen; $R^1$ represents hydrogen or $(C_1-C_4)$alkyl, $R^2$ represents a wholly saturated nitrogen containing 5–6 membered heterocyclic ring which may contain a further N atom wherein 1 to 3 of the ring carbons may optionally bear $(C_1-C_4)$alkyl substituents, one of the ring nitrogens may optionally bear a substituent $R^5$ representing $(C_1-C_4)$alkyl and two of the ring members are bridged by an alkylene chain of 1 to 3 carbon atoms wherein one of the methylene groups may optionally be replaced by —NH— or

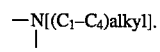

or a group -alk-W wherein alk represents a linear alkylene chain of 1 to 3 carbon atoms and W is a wholly saturated nitrogen containing 5–6 membered heterocyclic ring defined as in the paragraph immediately above.

Another group of preferred compounds of the invention is represented by those compounds wherein A, B, and M either represents the sugar moieties as above defined or each simultaneously represents a hydrogen atom.

A subgroup of compounds of the invention is represented by those compounds of formula I wherein A represents beta-D-2-deoxy-2-(8-methylnonanoyl)-amino-glucopyranosyl, B represents beta-D-2-deoxy-2-acetylamino-glucopyranosyl and M represents alpha-D-mannopyranosyl.

Other most preferred compounds are those of formula I wherein A, B and M either simultaneously represent the sugar moieties defined above or each simultaneously represent a hydrogen atom, R represents hydrogen, and $NR^1R^2$ represents a group —HN(alk)W wherein "alk" represents a linear alkylene chain of 2, 3; 4, 5, 6, 7 or 8 methylene units and W represents a group selected from: —$NH_2$, —$NHCH_3$, —$NHC_2H_5$, —$N(CH_3)_2$, —$N(C_2H_5)_2$, and —$N(CH_3)(C_2H_5)$, or a group —$HNCH(COOCH_3)(CH_2)_4NH_2$,

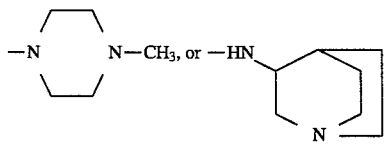

A subgroup of compounds of the invention is represented by those compounds of formula I wherein R represents hydrogen or a protecting group of the amine function, Y represents a group —$NR^1R^2$ wherein $R^1$ represents hydrogen, $(C_1-C_6)$alkyl, hydroxy $(C_2-C_4)$alkyl, halogeno$(C_2-C_4)$alkyl, $(C_1-C_4)$alkoxy$(C_2-C_4)$alkyl, amino$(C_2-C_4)$alkyl, $(C_1-C_4)$alkylamino$(C_2-C_4)$alkyl, di$(C_1-C_4)$alkylamino$(C_2-C_4)$alkyl, $R^2$ represents hydrogen, $(C_1-C_6)$alkyl, hydroxy$(C_2-C_4)$alkyl, halogeno$(C_2-C_4)$alkyl, $(C_1-C_4)$alkoxy $(C_2-C_4)$alkyl, a nitrogen containing 5–6 membered heterocyclic ring which may be unsaturated, partially saturated or wholly saturated and may contain 1 to 3 further heteroatoms selected from N, S, and O wherein one of the ring nitrogens may optionally bear a substituent $R^5$ selected from $(C_1-C_4)$alkyl, $(C_4-C_7)$cycloalkyl, phenyl optionally substituted with halogen or $(C_1-C_4)$alkyl, phenyl$(C_1-C_4)$alkyl, pyridyl, and $(C_1-C_4)$alkylpyridinium; a group -alk-W wherein "alk" represents a linear alkylene chain of 1 to 6 carbon atoms which is optionally substituted with a substituent selected from $(C_1-C_4)$alkyl, hydroxy$(C_1-C_4)$alkyl, hydroxy, carboxy, aminocarbonyl, $(C_1-C_4)$alkylaminocarbonyl, di$(C_1-C_4)$alkylaminocarbonyl, $(C_1-C_4)$alkoxycarbonyl, phenyl$(C_1-C_4)$alkoxycarbonyl, and W represents a carboxy, $(C_1-C_4)$alkoxycarbonyl, phenyl$(C_1-C_4)$alkoxycarbonyl, aminocarbonyl, $(C_1-C_4)$alkylaminocarbonyl, di$(C_1-C_4)$alkylaminocarbonyl, pentosaminocarbonyl, hexosaminocarbonyl, ureido, guanidino, a nitrogen containing 5–6 membered heterocyclic ring defined as above, a group of the formula —$NR^3R^4$ wherein $R^3$ and $R^4$ each independently represent hydrogen, $(C_1-C_6)$alkyl, hydroxy$(C_2-C_4)$alkyl and halogeno$(C_2-C_4)$alkyl, or $R^4$ represents phenylmethyloxycarbonyl and $R^3$ represents hydrogen; a group of the formula

—$N^{(+)}R^6R^7R^8$ wherein $R^6$, $R^7$ and $R^8$ each independently represent $(C_1-C_4)$alkyl, or $R^1$ and $R^2$ taken together with the adjacent nitrogen atom represent a saturated 5–7 membered heterocyclic ring which may optionally bear one to two $(C_1-C_4)$alkyl substituents on the ring carbons and may contain a further heterogroup selected from —O—, —S—, and —$NR^5$— wherein $R^5$ is defined as above.

Representative examples of the compounds of the invention include those compounds of formula I wherein R is hydrogen, A, B, and M are as defined above and

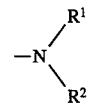

represents: —$NH_2$, —$NHC_4H_9$, —$NH(CH_2)_4$—OH, —$NHCH_2COOH$, —$NHCH_2COOCH_2C_6H_5$, —$NHCH_2COOC_2H_5$, —NH—$CH_2CONH_2$, —NH—$CH_2$—$CON(C_2H_5)_2$, —NH—CH—COOH, —NH—CHCONH$_2$
     |                        |
    COOH          CONH$_2$ —NH—CH—COOC$_2$H$_5$, —NHCH(CH$_2$)$_m$CONH$_2$,
     |                         |
  COOC$_2$H$_5$        COOH —NHCH—(CH$_2$)$_m$CONH$_2$, —NHCH(CH$_2$)$_m$COOH,
     |                       |
   COOH         CON(CH$_3$)$_2$ wherein m represents the integer 1, 2, 3 or 4, —NH—(CH$_2$)$_n$—NH$_2$, —NH—(CH$_2$)$_n$NHCH$_3$,
—NH(CH$_2$)$_n$—N(CH$_3$)$_2$, —NH—(CH$_2$)$_n$N(C$_2$H$_5$)$_2$,
—HN(CH$_2$)$_n$N(CH$_3$)(C$_2$H$_5$)
wherein n represents 2, 3, 4, 5, 6, 7 or 8
—NH—(CH$_2$)$_2$N(C$_2$H$_4$OH)(C$_2$H$_4$Cl);
—NH(CH$_2$)$_2$N[(CH$_2$)$_4$OH]$_2$, —NH(CH$_2$)$_4$N(C$_2$H$_4$Cl)$_2$, —NH—(CH$_2$)$_3$N(C$_4$H$_9$)$_2$, —NH—(CH$_2$)$_3$$\overset{\oplus}{N}$(CH$_3$)$_3$,

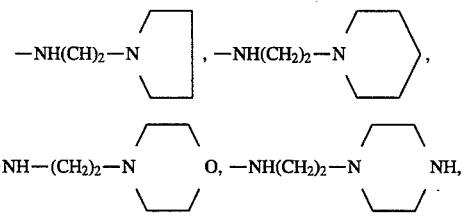

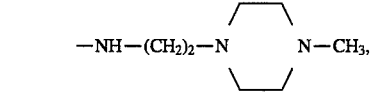

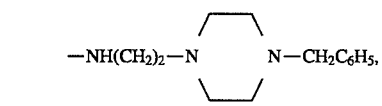

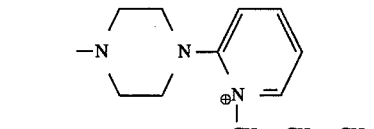

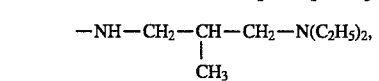

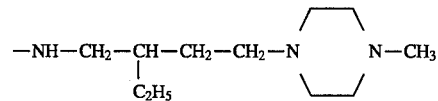

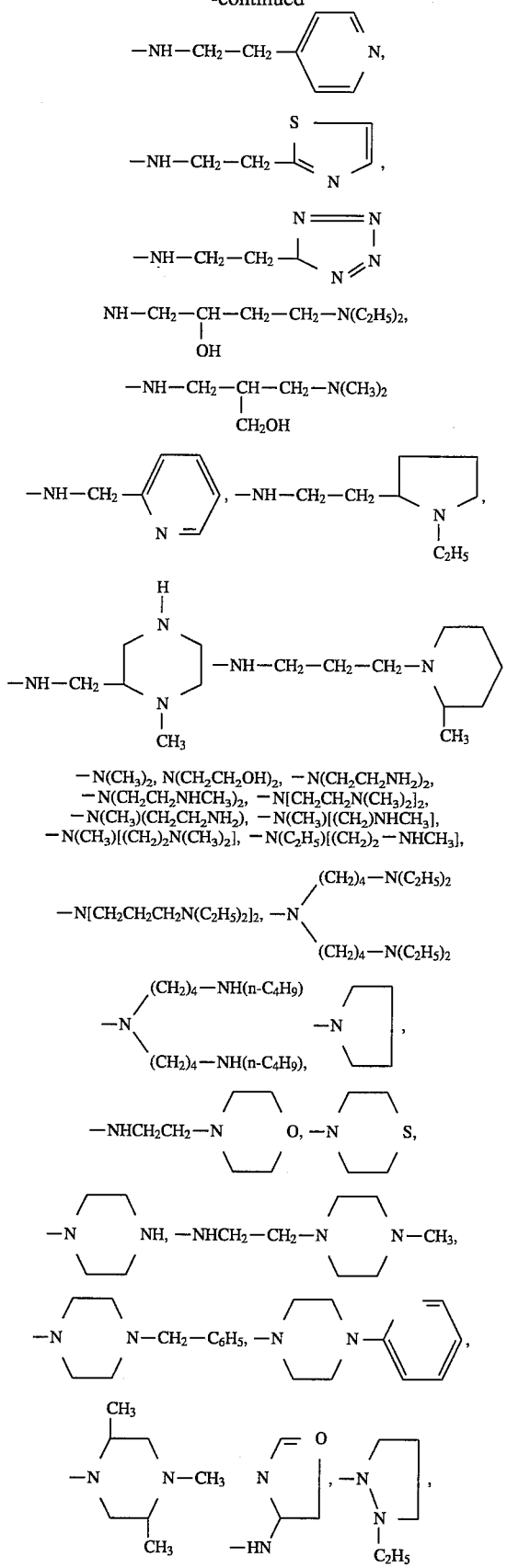
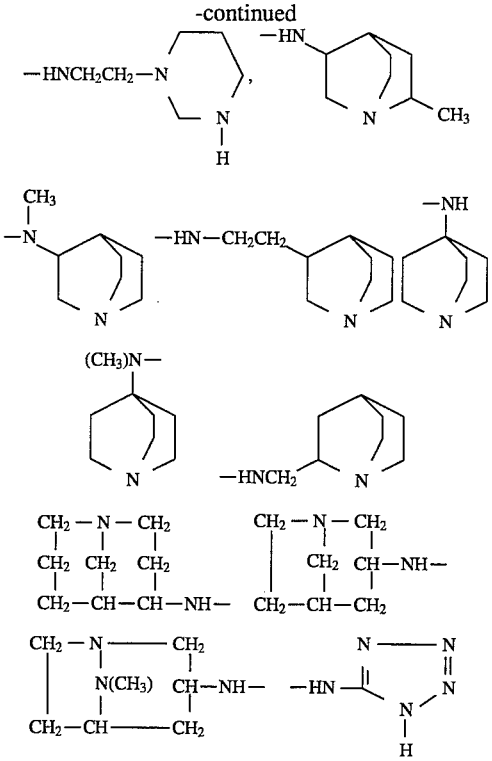

The compounds of the invention can form salts according to conventional procedures. In particular, those compounds of formula I wherein R represent hydrogen as well as those compounds of formula I wherein the group —NR$^1$R$^2$ contains further amine functions form acid addition salts. In addition, those compounds of the invention which contain acid functions in the —NR$^1$R$^2$ moiety may also form base addition salts. In general, those compounds of the invention which contain acid and basic functions can form internal salts. For the scope of the present invention the "internal salts" are encompassed by the definition of the "non-salt" form. Preferred addition salts of the compounds of this invention are the pharmaceutically acceptable acid and/or base addition salts. With the term "pharmaceutically acceptable acid and/or base addition salts" are intended those salts with acids and/or bases which from biological, manufacturing and formulation standpoint are compatible with the pharmaceutical practice as well as with the use in the animal growth promotion. Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids. Representative examples of theses bases are: alkali metal or alkaline-earth metal hydroxide such sodium, potassium, and calcium hydroxide; ammonia and organic aliphatic, alicyclic or aromatic amines such as methylamine, dimethylamine, trimethylamine, and picoline. When the compounds of the invention contain a (C$_1$-C$_4$)alkyl or a —N$^\oplus$R$^6$R$^7$R$^8$ moiety wherein R$^6$, R$^7$ and R$^8$ have the same meanings as above, the respective anion is an anion derived from a pharmaceutically acceptable acid.

Representative examples of said anion are those deriving from the acids listed above. The transformation of the free amino or non-salt compounds of the invention into the corresponding addition salts, and the reverse, i.e. the transformation of an addition salt of a compound of the invention into the non-salt or free amino form, are within the ordinary technical skill and are encompassed by the present invention. For instance, a compound of formula I can be transformed into the corresponding acid or base addition-salt by dissolving the non-salt form in an aqueous solvent and adding a slight molar excess of the selected acid or base. The resulting solution or suspension is then lyophilized to recover the desired salt. Instead of lyophilizing, in some instances, it is possible to recover the final salt by extraction with an organic solvent, concentration to a small volume of the separated organic phase and precipitation by adding a non-solvent. In case the final salt is unsoluble in an organic solvent where the non-salt form is soluble it is recovered by filtration from the organic solution of the non-salt form after addition of the stoichiometric amount or a slight molar excess of the selected acid or base. The non-salt form can be prepared from a corresponding acid or base salt dissolved in an aqueous solvent which is then neutralized to free the non-salt form. This is then recovered for instance by extraction with an organic solvent or is transformed into another base or acid addition salt by adding the selected acid or base and working up as above. When following the neutralization desalting is necessary, a common desalting procedure may be employed. For example, column chromatography on controlled pore polydextrane resins (such as SEPHADEX LH 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water from 50:50 to about 100% acetonitrile.

As is known in the art, the salt formation either with pharmaceutically acceptable acids (bases) or non-pharmaceutically acceptable acids (bases) may be used as a convenient purification technique. After formation and isolation, the salt form of a compound of formula I can be transformed into the corresponding non-salt or into a pharmaceutically acceptable salt.

In some instances the acid addition salt of a compound of formula I is more soluble in water and hydrophilic solvents and has an increased chemical stability.

However, in view of the similarity of the properties of the compounds of formula I and their salts, what is said in the present application when dealing with the biological activities of the compounds of formula I applies also to their pharmaceutically acceptable salts, and viceversa.

The compounds of the invention are useful as semi-synthetic antibacterial agents mainly active against gram positive bacteria, but also active against gram negative bacteria. The compounds of the invention wherein R is different from hydrogen while possessing a certain antimicrobial activity are mainly useful as intermediates for those compounds of formula I wherein R is hydrogen.

A general procedure for preparing a compound of the invention is represented by the reaction (amidation) of a suitable teicoplanin starting material as above defined with the selected amine of formula $HNR^1R^2$ wherein $R^1$ and $R^2$ have the same meanings as above in an inert organic solvent in the presence of a condensing agent. When teicoplanin or teicoplanin $A_2$ complex is used as the starting material, the relative amide of formula I obtained according to the amidation reaction of this invention is a mixture of five amide derivatives corresponding to the five main components of teicoplanin $A_2$ as mentioned above. Said mixture may be separated into the five single amide derivatives according to the techniques analogously known in the art (see for instance British Patent Application Publication No. 2121401). For clarity, both the mixture itself as obtained from the amidation reaction and each of the five amide derivatives are intended to form part of this invention as claimed here with the meaning of A representing —N[($C_{10}$–$C_{11}$)aliphatic acyl] -β-D-2-deoxy-2-amino-glucopyranosyl. Conversely, the single pure amide derivatives of each teicoplanin $A_2$ component is obtained by following the process of the invention starting from the single component itself instead of starting from the complex.

In carrying out the amidation for preparing the compounds of this invention, sometimes, and especially when at least one of A, B, and M in the teicoplanin starting material represent hydrogen, it is convenient to protect the primary amino function of the teicoplanin starting material in order to reduce possible undesired side-reactions. Also, when the amine $HNR^1R^2$ contains further reactive functions such as amino or carboxy groups, which may unfavorably interfere with the course of the amidation they are protected by methods known per se in the art such as those described in reference books like T. W. Greene, "Protective Groups in Organic Synthesis", John Wiley and Sons, New York, 1981, and M. Mc. Omie "Protecting Groups in Organic Chemistry" Plenum Press, New York, 1973. These protecting groups must be stable at the conditions of the reaction process, must not unfavorably interfere with the main amidation reaction, and must be easily cleavable and removable from the reaction medium at the end of the reaction without altering the newly formed amide bond.

Representative examples of N-protecting groups which may be advantageously used in the process of the invention for protecting an amino function both in the teicoplanin starting material and, when appropriate, in the $R^1$ and $R^2$ moiety of the amine $HNR^1R^2$ are carbamate forming reagents characterized by the following oxycarbonyl groups: 1,1-dimethylpropynyloxycarbonyl, t-butyloxycarbonyl, vinyloxycarbonyl, aryloxycarbonyl, cinnamyloxycarbonyl, benzyloxycarbonyl, p-nitrobenzyloxycarbonyl,3,4-dimethoxy 6-nitrobenzyloxycarbonyl, 2,4-dichlorobenzyloxycarbonyl, 5-benzisoxazolylmethyloxycarbonyl, 9-anthranylmethyloxycarbonyl, diphenylmethyloxycarbonyl, isonicotinyloxycarbonyl, S-benzyloxycarbonyl, and the like.

Other suitable N-protecting agents are aldehydes or ketones, or derivatives thereof which are capable of forming Schiff bases with the amino group of the teicoplanin nucleus to be protected. Preferred examples of such Schiff base forming agents are benzaldehydes and particularly preferred is 2-hydroxybenzaldehyde (salicylaldehyde).

A convenient means of protection in the case the amine reactant $HNR^1R^2$ contains a primary amino function as substituent for $R^1$ and/or $R^2$ is in some instances, the formation of a benzyliden derivative which may be prepared by reacting the amine $HNR^1R^2$ with benzaldehyde in a lower alkanol, such as ethanol, preferably at room temperature. After the reaction with the selected teicoplanin starting material has been completed, the benzylidene protecting group may be removed as known in the art, e.g. by treating with diluted mineral acid, preferably hydrochloric acid, at room temperature. Obviously, when the final compound of formula I contains groups which are labile under acidic conditions, e.g. when A, B or M represent sugar moieties as above defined which may be hydrolized in an acidic medium, other removal conditions must be used, such as catalytic hydrogenation using for instance Palladium on carbon as the catalyst to remove the proper protecting group. In this case, however, attention should be paid to the presence of groups which may be modified by catalytic hydrogenation. A typical consequence of the catalytic hydrogenation of a derivative of formula I wherein A represents a group as above defined whose acyl portion is Z-decenoyl (i.e. a teicoplanin $A_2$ component 1 derivative or a mixture containing it) is that it is at least partially transformed into the corresponding decanoyl derivative (i.e. a derivative of teicoplanin $A_2$ component 3). The man skilled in the art is capable, also on the basis of the present disclosure, of deciding which functions of the amine $HNR^1R^2$ need to be protected, how they must be protected and the proper deprotection reaction which is necessary to free the final compound. For instance, a suitable protection for reactive carboxylic acid function is by forming an ester function.

As it is appreciated by the skilled technicians, the ultimate choice of the specific protecting group depends on the characteristics of the particular amide derivative which is desired. In fact, this amide function of the final compound should be stable at the condition of removal of the protecting group(s). Since the conditions of removal of the different protecting groups are known, the skilled technician is capable of selecting the proper protecting group. For instance, where the final compound possess also a benzyl ester function or N-benzyl function, the protecting groups which are usually removable by catalytic hydrogenation, such as the benzyloxycarbonyl group, should be avoided, while those protecting groups which are removable under acidic conditions, such as t.butoxycarbonyl, can be conveniently used. On the contrary, catalytic hydrogenation may be conveniently used in a case like the above when it is desired to convert a compound of formula I containing said N-benzyl or benzyl ester function in the —$NR^1R^2$ moiety into the corresponding compound wherein said N-benzyl or benzyl ester function is replaced by a hydrogen atom.

Inert organic solvents useful for the condensation reaction are those organic aprotic solvents which do not unfavorably interfere with the reaction course and are capable of at least partially solubilizing the teicoplanin starting material. Examples of said inert organic solvents are organic amides, alkyl ethers, ethers of glycols and polyols, phosphoramides, sulfoxides and aromatic compounds. Preferred examples of inert organic solvents are: dimethylformamide, dimethoxyethane, hexamethylphosphoramide, dimethylsulfoxide, benzene, toluene and mixtures thereof.

The condensing agent in the process of the invention is one suitable for forming amide bonds in organic compounds and in particular in peptide synthesis. Representative and preferred examples of condensing agents are ($C_1$–$C_4$)alkyl, phenyl or heterocyclic phosphorazidates such as, diphenyl phosphorazidate (DPPA), diethyl phosphorazidate, di(4-nitrophenyl)phosphorazidate, dimorpholylphosphorazidate and diphenylphosphorochloridate. The preferred condensing agent is diphenyl phosphorazidate (DPPA).

In the process of the invention, the amine reactant $HNR^1R^2$ is normally used in a molar excess. In general, a 2- to 6-fold molar excess is used while a 3 to 4-fold molar excess is preferred. For the amidation to proceed, it is necessary that the amine $HNR^1R^2$ be capable of forming a salt with the carboxy function of the teicoplanin starting material. In case the amine $HNR^1R^2$ is not strong enough to form such a salt in the selected reaction medium, it is necessary to add a salt-forming base to the reaction mixture at least in an equimolecular amount with the teicoplanin starting material. Examples of said salt-forming bases are tertiary organic aliphatic or alicyclic amines such as trimethylamine, triethylamine, N-methyl pyrrolidine or heterocyclic bases such as picoline, and the like. The condensing agent is generally employed in a slight molar excess such as from 1.2 to 1.7 and preferably is 1.5 times the teicoplanin starting compound. In addition, the amine reactant $HNR^1R^2$ may also conveniently be introduced in the reaction medium as a corresponding acid addition salt, e.g. the hydrochloride. In this case, at least a double molar proportion and preferably a 2 to 4 fold molar excess of a strong base capable of freeing the $HNR^1R^2$ amine from its salts, is used. Also in this case, the suitable base is a tertiary organic aliphatic or alicyclic amine like those exemplified above. In fact, at least in some instances, the use of salt of the amine $HNR^1R^2$ which is then freed in situ with the above mentioned bases, is greatly preferred especially when the salt is more stable than the corresponding free amine.

The reaction temperature will vary considerably depending on the specific starting materials and reaction conditions. In general, it is preferred to conduct the reaction at temperatures between 0°–20° C. Also the reaction time vary considerably depending on the other reaction parameters. In general the condensation reaction is completed in about 24–48 h. In any case, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques which include for instance extraction with solvents, precipitation by addition of non-solvents, etc., in conjunction with further separations and purifications by column chromatography. As already said, when protection of the $HNR^1R^2$ reactant or of the teicoplanin starting material, or of both of them, is necessary, the protected final compound is then de-protected according to procedures which are known per se and mainly depends on the protecting group involved. In case both the amine $HNR^1R^2$ and the teicoplanin starting material are protected, it might be convenient to use a similar type of protection which may be removed under the same conditions, so that only one de-protection step is needed to free both functions.

It is also evident that in many instances a compound of the invention may be prepared in more than one way and that a compound of the invention may be transformed into another by means of known per se reactions. For instance, when the $HNR^1R^2$ amine is a diamine compound such as $HN(R^1)$-alk—$NR^3R^4$ defined above, the desired amine compound of formula I may be prepared either directly by condensing said amine, conveniently protected if necessary, with the selected starting material or it can be prepared by reacting an amide of formula I wherein the substituent $R^2$ is alk-halo, wherein halo is preferably a chlorine or bromine atom with an amine of formula $HNR^3R^4$. Moreover, an amide compound of formula I, bearing a carboxy function on the —$NR^1R^2$ moiety may be transformed into the corresponding amide or substituted amide derivative by usual techniques. Moreover, said carboxy function may also be transformed into the corresponding ester of acyl halide function by usual techniques. More particularly, an ester function is in general formed by reacting the carboxy containing product with a preparation of an alcohol in the presence of an acid catalyst at a temperature varying between room temperature and the boiling point of the reaction mixture. The acid is preferably a minerals acid and the alcohol contains the moiety that is to be linked to the carboxylic function in the ester derivative.

An inert solvent may also by used. Obviously, a compound of formula I bearing a carboxylic ester function on the —NR$^1$R$^2$ substituent may be transformed into the corresponding carboxylic compound by hydrolysis. A preferred hydrolysis technique involves an aqueous solution of an alkali metal carbonate, like sodium or potassium carbonate, at a temperature from room temperature to the boiling point of the reaction mixture. A compound of formula I bearing an —NH$_2$ function on the —NR$^1$R$^2$ moiety may be transformed into the corresponding monoalkylamino derivative by means of a "reductive alkylation" which involves reacting it with the selected carbonyl derivative (which is capable of giving the desired alkyl substituent upon reduction) to form the corresponding Schiff base intermediate which is then reduced in the presence of a suitable reducing agent such as sodium or potassium borohydride. When a free amino group is present in the =NR$^1$R$^2$ moiety of formula I, it may be alkylated as known in the art, e.g. by reacting it, or possibly the corresponding compound wherein the primary amino group of the teicoplanin moiety has been protected, with an alkyl halide (bromide, chloride or iodide). Likewise, a secondary amino function may be transformed into a tertiary one or a tertiary amino function may be quaternized. In addition, the sugar moiety of an amide compound of formula I may be selectively removed to transform it into another amide compound of formula I. For example, an amide compound of formula I wherein A, B, and M represent a sugar moiety as above defined can be transformed into the corresponding compound wherein B and M are as above and A is hydrogen by means of controlled acid hydrolysis in a strong concentrated aqueous organic acid. The concentrated organic acid in this case is preferably aqueous trifluoroacetic acid at a concentration between 75% and 95%, and the reaction temperature is preferably between 10° and 50° C. The preferred hydrolysis conditions are represented by about 90% trifluoroacetic acid at room temperature. The reaction time varies depending on the other specific reaction parameters but, in any case, the reaction may be monitored by TLC or preferably HPLC techniques. An analogous selective hydrolysis is reported in European Patent Application No 84114559.2.

Similarly, amide compounds of formula I wherein A, B, and M represent a sugar moiety as above defined or A represents hydrogen and B and M represent sugar moieties as above defined can be transformed into the corresponding amide compounds of formula I wherein A and M represent hydrogen and B represent a sugar moiety as defined by means of a selective hydrolysis with a strong acid in the presence of a polar aprotic solvent selected from ethers, ketones, and mixture thereof which are liquid at room temperature. Preferred hydrolysis conditions are in this case represented by the use of a concentrated mineral acid in the presence of an ether such as dimethoxyethane at room temperature. Also in this case, the reaction course may be monitored by TLC or preferably HPLC. An analogous selective hydrolysis is reported in European Patent Application No. 85109495.

According to another embodiment of the present invention, an amide compound of formula I wherein A, B and M represents sugar moieties as defined above, an amide compound of formula I wherein A represents hydrogen and B and M represent the above defined sugar moieties, or an amide compound of formula I wherein A and M represent hydrogen, and B represents a sugar moiety as above defined may be transformed into the corresponding amide compound of formula I wherein A, B and M represents hydrogen atoms by means of a selective hydrolysis in an organic protic solvent selected from aliphatic acids and alpha-halogenated aliphatic acids which at the reaction temperature are liquids, aliphatic and cycloaliphatic alkanols which at the reaction temperature are liquids slightly mixable with water, phenyl-substituted lower alkanols wherein the phenyl moiety may optionally carry (C$_1$-C$_4$)alkyl, (C$_1$-C$_4$)alkoxy or halo rests which at the reaction temperature are liquids slightly mixable with water, and beta-polyhalogenated lower alkanols, which at the reaction temperature are liquids; in the presence of a strong acid, compatible with the solvent, selected from strong mineral acids, strong organic acids and strong acid cation exchange resins in the hydrogen form and at a temperature between 20° C. and 100° C. In this case, the preferred hydrolysis conditions are represented by the use of a mineral acid, such as hydrochloric acid, in an haloalkanol such as trifluoroethanol, at a temperature between 65° C. and 85° C. Analogous selective hydrolysis conditions on a similar substrate are described in European Patent Application No. 84114558.4.

In the following table (Table I) the structure formulas of representative examples of compounds of the invention are reported.

TABLE I

| Compound | A | B | M | R | —NR$^1$R$^2$ |
|---|---|---|---|---|---|
| 1 | —GNHCOR$_{(1-5)}$ | —GNHCOCH$_3$ | —M | H | —NH(CH$_2$)$_3$N(CH$_3$)$_2$ |
| 2a | " | " | " | " | —NH(CH$_2$)$_3$N(C$_2$H$_5$)$_2$ |
| 2b | —GNHCOR$_{(2)}$ | " | " | " | " |
| 3 | —GNHCOR$_{(1-5)}$ | " | " | " | —NH(CH$_2$)$_3$N(n-C$_4$H$_9$)$_2$ |
| 4 | " | " | " | " | 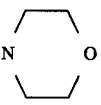 —NH(CH$_2$)$_2$—N⟨O⟩ |
| 5 | " | " | " | " |  —NH(CH$_2$)$_2$—N⟨ ⟩ |

TABLE I-continued

| Compound | A | B | M | R | —NR¹R² |
|---|---|---|---|---|---|
| 6 | " | " | " | " | —N(piperazine)N—CH₃ |
| 7 | H | —GNHCOCH₃ | —M | H | —NH(CH₂)₃N(CH₃)₂ |
| 8 | " | " | " | " | —NH(CH₂)₃N(C₂H₅)₂ |
| 9 | " | " | " | " | —NH(CH₂)₃N(n-C₄H₉)₂ |
| 10 | " | " | " | " | —NH(CH₂)₂—N(morpholino)O |
| 11 | " | " | " | " | —NH(CH₂)₂N(piperidino) |
| 12 | " | " | " | " | —N(piperazine)N—CH₃ |
| 13 | " | " | H | " | —NH(CH₂)₃N(CH₃)₂ |
| 14 | " | " | " | " | —NH(CH₂)₂—N(morpholino)O |
| 15 | H | —GNHCOCH₃ | H | H | —NH(CH₂)₂—N(morpholino)O |
| 16 | " | " | " | " | —NHCH₂COOC₂H₅ |
| 17 | " | " | " | " | —NHCH₂COOCH₃ |
| 18 | " | H | " | " | —NH(CH₂)₃N(CH₃)₂ |
| 19 | " | " | " | " | —NH(CH₂)₃N(C₂H₅)₂ |
| 20 | " | " | " | " | —NH(CH₂)₃N(n-C₄H₉)₂ |
| 21 | " | " | " | " | —NH(CH₂)₂—N(morpholino)O |
| 22 | " | " | " | " | —NH(CH₂)₂—N(piperidino) |
| 23 | H | H | H | H | —N(piperazine)N—CH₃ |
| 24 | " | " | " | " | —N(piperazine)N-(2-pyridyl) |
| 25 | " | " | " | " | —N(morpholino)O |
| 26 | —GNHCOR₍₁₋₅₎ | —GNHCOCH₃ | —M | " | —N(thiomorpholino)S |

TABLE I-continued

| Compound | A | B | M | R | —NR$^1$R$^2$ |
|---|---|---|---|---|---|
| 27 | —GNHCOR$_{(1-5)}$ | —GNHCOCH$_3$ | —M | H | —NHCH(COOH)—(CH$_2$)$_4$NH$_2$ |
| 28 | H | " | " | " | —N(morpholine-S) |
| 29 | " | " | " | " | —NH—CH(COOH)—(CH$_2$)$_4$NH$_2$ |
| 30 | " | H | H | " | —NH(CH$_2$)$_2$N(CH$_2$CH$_2$OH)(CH$_2$CH$_2$Cl) |
| 31 | H | H | H | H | —NH(CH$_2$)$_5$CO—NH—[glucosamine] |
| 32a | —GNHCOR$_{(1-5)}$ | —GNHCOCH$_3$ | —M | " | —NH—CH(COOH)(CH$_2$)$_3$NHC(=NH)—NH$_2$ |
| 32b | —GNHCOR$_{(2,3)}$ | " | " | " | —NH—CH(COOH)(CH$_2$)$_3$NHC(=NH)—NH$_2$ |
| 32c | —GNHCOR$_{(4,5)}$ | " | " | " | —NH—CH(COOH)(CH$_2$)$_3$NHC(=NH)—NH$_2$ |
| 33 | —GNHCOR$_{(1-5)}$ | —GNHCOCH$_3$ | —M | H | —NH—CH(COOCH$_3$)(CH$_2$)$_3$NHC(=NH)—NH$_2$ |
| 34 | " | " | " | " | —HN(CH$_2$)$_3$N(C$_5$H$_{11}$)$_2$ |
| 35 | " | " | " | " | —HN(CH$_2$)$_3$N(C$_6$H$_{13}$)$_2$ |
| 36 | " | " | " | " | —NH(CH$_2$)$_4$—CHNH$_2$(COOH) |
| 37 | " | " | " | " | —NH(CH$_2$)$_4$CHNH$_2$(COOCH$_3$) |
| 38 | " | " | " | " | —NHCH$_2$COOCH$_3$ |
| 39 | —GNHCOR$_{(1-5)}$ | —GNHCOCH$_3$ | —M | H | —NHCH(COOH)(CH$_2$)$_2$COOH |
| 40 | " | " | " | " | —NHCH(COOH)(CH$_2$)$_2$CONH$_2$ |
| 41 | H | " | " | " | —NHCH(COOH)(CH$_2$)$_3$NHC(=NH)—NH$_2$ |

TABLE I-continued

| Compound | A | B | M | R | $-NR^1R^2$ |
|---|---|---|---|---|---|
| 42 | " | " | " | " | $-NHCH(CH_2)_3NHC(=NH)-NH_2$ with COOCH$_3$ on CH |
| 43 | H | $-GNHCOCH_3$ | $-M$ | H | $-NH(CH_2)_3N(C_5H_{11})_2$ |
| 44 | " | " | " | " | $-NH(CH_2)_3N(C_6H_{13})_2$ |
| 45 | " | " | " | " | $-NH(CH_2)_4-CHNH_2$ with COOH |
| 46 | " | " | " | " | $-NH(CH_2)_4-CHNH_2$ with COOCH$_3$ |
| 47 | H | $-GNHCOCH_3$ | $-M$ | H | $-NHCH_2COOCH_3$ |
| 48 | " | " | " | " | $-NHCH(CH_2)_2COOH$ with COOH |
| 49 | " | " | " | " | $-NHCH(CH_2)_2CONH_2$ with COOH |
| 50 | H | GNHCOCH$_3$ | H | H | $-NHCH(CH_2)_3NHC(=NH)-NH_2$ with COOH |
| 51 | " | " | " | " | $-NHCH(CH_2)_4NH_2$ with COOC$_2$H$_5$ |
| 52 | " | " | " | " | $-HN(CH_2)_3N(C_5H_{11})_2$ |
| 53 | H | GNHCOCH$_3$ | H | H | $-HN(CH_2)_3N(C_6H_{13})_2$ |
| 54 | " | " | " | " | $-NH(CH_2)_4-CHNH_2$ with COOCH$_3$ |
| 55 | " | " | " | " | $-NH(CH_2)_4-CHNH_2$ with COOH |
| 56 | " | " | " | " | $-NHCH_2COOH$ |
| 57 | H | $-GNHCOCH_3$ | H | H | $-NHCH(CH_2)_2COOH$ with COOH |
| 58 | " | " | " | " | $-NHCH(CH_2)_2CONH_2$ with COOH |
| 59 | " | H | " | " | $-NHCH(CH_2)_3NHC(=NH)-NH_2$ with COOH |
| 60 | " | " | " | " | $-NHCH(CH_2)_3NHC(=NH)-NH_2$ with COOCH$_3$ |
| 61 | H | H | H | H | $-NH(CH_2)_3N(C_5H_{11})_2$ |
| 62 | " | " | " | " | $-NH(CH_2)_3N(C_6H_{13})_2$ |
| 63 | " | " | " | " | $-NH(CH_2)_4CHNH_2$ with COOCH$_3$ |
| 64 | " | " | " | " | $-NH(CH_2)_4CHNH_2$ with COOH |
| 65 | H | H | H | H | $-NHCH_2COOH$ |

TABLE I-continued

| Compound | A | B | M | R | $-NR^1R^2$ |
|---|---|---|---|---|---|
| 66 | " | " | " | " | $-NHCH(CH_2)_2COOH$ with COOH branch |
| 67 | " | " | " | " | $-NHCH(CH_2)_2CONH_2$ with COOH branch |
| 68 | $-GNHCOR_{(1-5)}$ | $-GNHCOCH_3$ | $-M$ | H | $-NH-CH(CH_2)_4NHCOOCH_2-C_6H_5$ with $COOCH_3$ branch |
| 69 | $-GNHCOR_{(1-5)}$ | $-GNHCOCH_3$ | $-M$ | H | $-NH-CH(CH_2)_4NHCOOCH_2-C_6H_5$ with COOH branch |
| 70 | " | " | " | " | $-N-(CH_2)_2N(CH_3)_2$ with $CH_3$ branch |
| 71 | $-GNHCOR_{(2,3)}$ | " | " | " | $-NH-CH(CH_2)_4NH_2$ with $COOCH_3$ branch |
| 72 | $-GNHCOR_{(1-5)}$ | $-GNHCOCH_3$ | $-M$ | $COOCH_2-C_6H_5$ | $-NH-CH(CH_2)_4NHCOOCH_2-C_6H_5$ with $COOCH_3$ branch |
| 73 | H | H | H | H | $-NH-CH(CH_2)_4NH_2$ with $COOCH_3$ branch |
| 74 | $-GNHCOR_{(1-5)}$ | $-GNHCOCH_3$ | $-M$ | H | $-NH-CH-(CH_2)_3-NH-C(=NH)-NH-NO_2$ with $COOCH_2-C_6H_5$ branch |
| 75 | $-GNHCOR_{(1-5)}$ | $-GNHCOCH_3$ | $-M$ | H | $-N(CH_3)_2$ |
| 76 | " | " | " | " | $-NH-CH_2-$(N-ethylpyrrolidin-2-yl) |
| 77 | " | " | " | " | $-NH(CH_2)_3-$(morpholin-4-yl) |
| 78 | H | H | H | H | $-NH(CH_2)_3-$(morpholin-4-yl) |
| 79 | H | H | H | H | $-NH-CH_2-$(N-ethylpyrrolidin-2-yl) |
| 80 | $-GNHCOR_{(1-5)}$ | $-GNHCOCH_3$ | $-M$ | " | $-NH(CH_2)_6NH_2$ |
| 81 | " | " | " | " | $-NH(CH_2)_4N(CH_3)_2$ |
| 81a | $-GNHCOR_{(2)}$ | " | " | " | " |
| 82 | $-GNHCOR_{(1-5)}$ | $-GNHCOCH_3$ | $-M$ | H | $-NH-$(quinuclidinyl) |
| 83 | H | H | H | H | $-NH-$(quinuclidinyl) |

TABLE I-continued

| Compound | A | B | M | R | $-NR^1R^2$ |
|---|---|---|---|---|---|
| 84 | " | " | " | " | $-NH-\underset{\underset{COOH}{\vert}}{CH}-(CH_2)_4-NH_2$ |
| 85 | $-GNHCOR_{(1-5)}$ | $-GNHCOCH_3$ | $-M$ | H | $-NH-CH_2-COOC_2H_5$ |
| 86 | " | " | " | " | $-NH-CH_2-COOH$ |
| 87 | " | " | " | " | $-NH(CH_2)_5N(CH_3)_2$ |
| 88 | " | " | " | " | $-NH(CH_2)_7N(CH_3)_2$ |
| 88a | $-GNHCOR_{(2)}$ | " | " | " | " |
| 89 | $-GNHCOR_{(1-5)}$ | $-GNHCOCH_3$ | M | H | $-NH-\langle\text{piperidine}\rangle N-CH_2-C_6H_5$ |
| 90 | " | " | M | H | $-NH-\langle\text{piperidine}\rangle N-H$ |
| 91 | " | " | " | " | $-NHCH_2-\langle\text{2-pyridyl}\rangle$ |
| 92 | " | " | " | " | $-\underset{\underset{COOCH_3}{\vert}}{NHCH}(CH_2)_3CH_3$ |
| 93 | H | H | H | H | $-\underset{\underset{CH_3}{\vert}}{N}-(CH_2)_2N(CH_3)_2$ |
| 94 | " | " | " | " | $-NH(CH_2)_2N(CH_3)_2$ |
| 94a | $-GNHCOR_{(2)}$ | " | " | " | " |
| 95 | $-GNHCOR_{(1-5)}$ | $-GNHCOCH_3$ | M | " | $-NH(CH_2)_2N(CH_3)_2$ |
| 96 | " | " | " | " | $-NH(CH_2)_4NH_2$ |
| 97 | H | H | H | H | $-NH(CH_2)_4N(CH_3)_2$ |
| 98 | " | " | " | " | $-NH-\underset{\underset{COOCH_2C_6H_5}{\vert}}{CH}(CH_2)_3NH\overset{\overset{NH}{\|}}{C}-NH_2$ |
| 99 | " | " | " | " | $-NH(CH_2)_4NH_2$ |
| 100 | H | H | H | H | $-NH(CH_2)_5N(CH_3)_2$ |
| 101 | " | " | " | " | $-NH(CH_2)_7N(CH_3)_2$ |
| 102 | " | " | " | " | $-NH(CH_2)_6NH_2$ |
| 103 | " | " | " | " | $-NH-\underset{\underset{COO-(n-C_4H_9)}{\vert}}{CH}(CH_2)_3NH\overset{\overset{NH}{\|}}{C}-NH_2$ |
| 104 | $-GNHCOR_{(1,5)}$ | $-GNHCOCH_3$ | $-M$ | " | $-NH-\underset{\underset{COOH}{\vert}}{CH}(CH_2)_3NH\overset{\overset{NH}{\|}}{C}-NH-NO_2$ |
| 105 | " | " | " | " | $-NH-\underset{\underset{COOCH_3}{\vert}}{CH}(CH_2)_3NH\overset{\overset{NH}{\|}}{C}-NH-NO_2$ |

Note:
—GNHCOR$_{(1-5)}$ = N[(C$_{10}$–C$_{11}$)aliphatic acyl]-β-D-2-deoxy-2-aminoglucopyranosyl
—GNHCOR$_{(2,3)}$ = N-(8-methylnonanoyl)-β-D-2-deoxy-2-aminoglucopyranosyl and N-decanoyl-β-D-2-deoxy-2-aminoglucopyranosyl
—GNHCOR$_{(4,5)}$ = N-(8-methyldecanoyl)-β-D-2-deoxy-2-aminoglucopyranosyl and N-(9-methyldecanoyl)-β-D-2-deoxy-2-aminoglucopyranosyl
—GNHCOCH$_3$ = N-acetyl-β-D-2-deoxy-2-aminoglucopyranosyl
—M = α-D-mannopyranosyl The following table (Table II) lists the methods of preparation, startings material and reaction yields of representative examples of compounds of the invention:

TABLE II

| Compound | Method of preparation | Starting material | | Yield % |
|---|---|---|---|---|
| 1 | $A_1$ | teicoplanin $A_2$ | $H_2N(CH_2)_3N(CH_3)_2$ | 46 |
| 2a | $A_1$ | teicoplanin $A_2$ | $H_2N(CH_2)_3N(C_2H_5)_2$ | 50 |
| 2b | A | teicoplanin $A_2$, component 2 | $H_2N(CH_2)_3N(C_2H_5)_2$ | 55 |
|  | G | compound 2a |  | 46 |
| 3 | $A_1$ | teicoplanin $A_2$ | $H_2N(CH_2)_3N(n\text{-}C_4H_9)_2$ | 42 |
| 4 | $A_1$ | teicoplanin $A_2$ | $H_2N(CH_2)_2\text{—N}\underset{\diagdown\_\_\_/}{\diagup^{\diagup\overline{\phantom{xx}}\diagdown}}O$ | 66 |
| 5 | $A_1$ | teicoplanin $A_2$ | $H_2N(CH_2)_2\text{—N}\underset{\diagdown\_\_\_/}{\diagup^{\diagup\overline{\phantom{xx}}}}$ | 61 |
| 6 | $A_1$ | teicoplanin $A_2$ | $HN\underset{\diagdown\_\_\_/}{\diagup^{\diagup\overline{\phantom{xx}}\diagdown}}N\text{—}CH_3$ | 47 |
| 7 | C | compound 1 | | 99 |
| 8 | C | Compound 2 | | 96 |
| 9 | C | Compound 3 | | 98 |
|  | $B_1$ | N—CBzO-antibiotic L 17054 | $H_2N(CH_2)_3N(n\text{-}C_4H_9)_2$ | 46 |
| 10 | C | Compound 4 | | 95 |
| 11 | C | Compound 5 | | 96 |
|  | $B_2$ | N-t-BOC-antibiotic L 17054 | $H_2N(CH_2)_2\text{—N}\underset{\diagdown\_\_\_/}{\diagup^{\diagup\overline{\phantom{xx}}}}$ | 55 |
| 12 | C | Compound 6 | | 94 |
| 13 | $A_2$ | Antibiotic L 17046 | $H_2N(CH_2)_3N(CH_3)_2$ | 53 |
|  | $B_1$ | N—CBzO-antibiotic L 17046 | $H_2N(CH_2)_3N(CH_3)_2$ | 32 |
|  | $D_1$ | Compound 1 | | 83 |
|  | $D_2$ | Compound 7 | | 88 |
| 14 | $D_1$ | Compound 4 | | 46 |
|  | $B_2$ | N-t-BOC-antibiotic L 17046 | $H_2N(CH_2)_2\text{—N}\underset{\diagdown\_\_\_/}{\diagup^{\diagup\overline{\phantom{xx}}\diagdown}}O$ | 48 |
| 15 | $D_1$ | Compound 11 | | 67 |
| 16 | $A_3$ | Antibiotic L 17046 | $H_2NCH_2COOC_2H_5(HCl)$ | 53 |
| 17 | $F_1$ | Compound 16 | | 78 |
| 18 | $A_2$ | Deglucoteicoplanin | $H_2N(CH_2)_3N(CH_3)_2$ | 16 |
|  | $B_2$ | N-t-BOC-deglucoteicoplanin | $H_2N(CH_2)_3N(CH_3)_2$ | 37 |
|  | $E_1$ | Compound 1 | | 61 |
|  | $E_2$ | Compound 7 | | 56 |
| 19 | $B_2$ | N-t-BOC-deglucoteicoplanin | $H_2C(CH_2)_3N(C_2H_5)_2$ | 51 |
|  | $E_1$ | Compound 2 | | 43 |
|  | $E_2$ | Compound 8 | | 46 |
| 20 | $B_2$ | N-t-BOC-deglucoteicoplanin | $H_2N(CH_2)_3N(n\text{-}C_4H_9)_2$ | 48 |
|  | $E_1$ | Compound 3 | | 56 |
|  | $E_2$ | Compound 3 | | 51 |
| 21 | $B_2$ | N-t-BOC-deglucoteicoplanin | $H_2N(CH_2)_2\text{—N}\underset{\diagdown\_\_\_/}{\diagup^{\diagup\overline{\phantom{xx}}\diagdown}}O$ | 39 |
|  | E | Compound 4 | | 37 |
|  | D* | Compound 4 | | 65 |
|  | E | Compound 14 | | 39 |
|  | D* | Compound 14 | | 65 |
| 22 | E | Compound 5 | | 44 |

TABLE II-continued

| Compound | Method of preparation | Starting material | | Yield % |
|---|---|---|---|---|
| | B$_1$ | N—CBzO-deglucoteicoplanin | H$_2$N(CH$_2$)$_2$—N⟨pyrrolidine⟩ | 24 |
| | B$_2$ | N-t-BOC-deglucoteicoplanin | HN⟨piperazine⟩N—CH$_3$ | 28 |
| | E$_2$ | Compound 12 | | 39 |
| 24 | B$_2$ | N-t-BOC-deglucoteicoplanin | HN⟨piperazine⟩N—(2-pyridyl) | 30 |
| 25 | B$_2$ | N-t-BOC-deglucoteicoplanin | HN⟨morpholine, O⟩ | 35 |
| 26 | A$_1$ | Teicoplanin A$_2$ | HN⟨thiomorpholine, S⟩ | 62 |
| 27 | A$_4$ | Teicoplanin A$_2$ | H$_2$N—CH(CH$_2$)$_4$NHCOOCH$_2$C$_6$H$_5$<br>\|<br>COOCH$_2$C$_6$H$_5$ | 41 |
| 28 | C | | Compound 26 | 90 |
| 29 | C | | Compound 27 | 90 |
| 30 | E$_2$ | | Compound 4 | 29 |
| 31 | B$_2$ | t-BOC-degluco-teicoplanin | sugar with CH$_2$OH, OH, HO, HO, H$_2$N(CH$_2$)$_5$CONH | 76 |
| 32a | A$_7$ | Teicoplanin A$_2$ | H$_2$NCH(CH$_2$)$_3$NHC(=NH)—NH—NO$_2$<br>\|<br>COOCH$_2$C$_6$H$_5$ | 38 |
| 32b | G | | Compound 32 | 64 |
| 32c | G | | Compound 32 | 56 |
| 33 | A$_6$ | Teicoplanin A$_2$ | H$_2$NCH(CH$_2$)$_3$NHC(=NH)—NH—NO$_2$<br>\|<br>COOCH$_3$ | 64 |
| 34 | A$_1$ | Teicoplanin A$_2$ | H$_2$N(CH$_2$)$_3$N(C$_5$H$_{11}$)$_2$ | ~50 |
| 35 | A$_1$ | Teicoplanin A$_2$ | H$_2$N(CH$_2$)$_3$N(C$_6$H$_{13}$)$_2$ | ~60 |
| 36 | A$_4$ | Teicoplanin A$_2$ | CBzO—NHCH(CH$_2$)$_4$NH$_2$<br>\|<br>COOCH$_2$C$_6$H$_5$ | ~30 |
| 37 | A$_4$ | Teicoplanin A$_2$ | CBzO—NHCH(CH$_2$)$_4$NH$_2$<br>\|<br>COOCH$_3$ | ~40 |
| 38 | A$_3$ | Teicoplanin A$_2$ | NH$_2$CH$_2$COOCH$_3$·HCl | ~45 |
| 39 | A$_4$ | Teicoplanin A$_2$ | H$_2$NCH(CH$_2$)$_2$COO-t-butyl<br>\|<br>COO—CH$_2$—C$_6$H$_5$ | ~70 |

TABLE II-continued

| Compound | Method of preparation | Starting material | | Yield % |
|---|---|---|---|---|
| 40 | F$_2$ | Teicoplanin A$_2$ | H$_2$NCH(CH$_2$)$_2$CONH$_2$<br>\|<br>COOCH$_3$ | ~25 |
| 41 | C | | Compound 32 | ~90 |
| 42 | C | | Compound 33 | ~90 |
| 43 | C | | Compound 34 | ~90 |
| 44 | C | | Compound 35 | ~90 |
| 45 | C | | Compound 36 | ~90 |
| 46 | C | | Compound 37 | ~90 |
| 47 | C | | Compound 38 | ~90 |
| 48 | C | | Compound 39 | ~90 |
| | A$_5$ | Antibiotic L 17054 | NH$_2$CH(CH$_2$)$_2$COOt-butyl<br>\|<br>COOt-butyl | ~50 |
| 49 | C | | Compound 40 | ~90 |
| 50 | D$_1$ | | Compound 41 | ~30 |
| 51 | F$_3$ | | Compound 27 | 30 |
| 52 | B$_2$ | t-BOC-antibiotic L 17046 | H$_2$N(CH$_2$)$_3$N(C$_5$H$_{11}$)$_2$ | ~55 |
| 53 | B$_2$ | t-BOC-antibiotic L 17046 | H$_2$N(CH$_2$)$_3$N(C$_6$H$_{13}$)$_2$ | ~60 |
| 54 | B$_1$ | CBzO-antibiotic L 17046 | CBzO—NHCH(CH$_2$)$_4$NH$_2$<br>\|<br>COOCH$_3$ | ~60 |
| 55 | F$_2$ | | Compound 54 | ~50 |
| 56 | B$_3$ | t-BOC-antibiotic L 17046 | NH$_2$CH$_2$COO-t-butyl | ~90 |
| 57 | A$_5$ | antibiotic L 17046 | NH$_2$CH(CH$_2$)$_2$COO-t-butyl<br>\|<br>COO-t-butyl | ~30 |
| | B$_3$ | t-BOC-antibiotic L 17046 | NH$_2$CH(CH$_2$)$_2$COO-t-butyl<br>\|<br>COO-t-butyl | ~60 |
| 58 | B$_1$ | t-BOC-antibiotic L 17046 | NH$_2$CH(CH$_2$)$_2$CONH$_2$<br>\|<br>COO-t-butyl | ~70 |
| 59 | B$_1$ | CBzO-deglucoteicoplanin | NH<br>\|\|<br>NH$_2$CH(CH$_2$)$_3$NHC—NH—NO$_2$<br>\|<br>COOCH$_2$C$_6$H$_5$ | ~40 |
| 60 | A$_7$ | CBzO-deglucoteicoplanin | NH<br>\|\|<br>NH$_2$CH(CH$_2$)$_3$NHC—NH—NO$_2$<br>\|<br>COOCH$_3$ | ~70 |
| 61 | B$_1$ | CBzO-deglucoteicoplanin | NH$_2$(CH$_2$)$_3$N(C$_5$H$_{11}$)$_2$ | ~65 |
| 62 | B$_1$ | CBzO-deglucoteicoplanin | NH$_2$(CH$_2$)$_3$N(C$_6$H$_{13}$)$_2$ | ~40 |
| 63 | B$_3$ | CBzO-deglucoteicoplanin | CBzO—NHCH(CH$_2$)$_4$NH$_2$<br>\|<br>COOCH$_3$ | ~60 |
| 64 | F$_2$ | | Compound 63 | 84 |
| 65 | B$_2$ | t-BOC-deglucoteicoplanin | NH$_2$CH$_2$COO-t-butyl | ~90 |
| 66 | B$_3$ | t-BOC-deglucoteicoplanin | NH$_2$CH(CH$_2$)$_2$COO-t-butyl<br>\|<br>COO-t-butyl | 87 |
| 67 | B$_2$ | t-BOC-deglucoteicoplanin | NH$_2$CH(CH$_2$)$_2$CONH$_2$<br>\|<br>COO-t-butyl | ~80 |
| 68 | B$_3$ | teicoplanin A$_2$ | H$_2$NCH(CH$_2$)$_4$NHCOOCH$_2$CH$_2$C$_6$H$_5$<br>\|<br>COOCH$_3$ | 87 |
| 69 | F$_2$ | | compound 68 | 92 |
| 70 | A$_2$ | teicoplanin A$_2$ | HN(CH$_2$)$_2$N(CH$_3$)$_2$<br>\|<br>CH$_3$ | 36 |

TABLE II-continued

| Compound | Method of preparation | Starting material | | Yield % |
|---|---|---|---|---|
| 71 | A₄ | teicoplanin A₂ | H₂N—CH(CH₂)₄NHCOOCH₂C₆H₅ <br> \| <br> COOCH₃ | 63 |
| 72 | B₃ | CBzO-degluco-teicoplanin | H₂N—CH(CH₂)₄NHCOOCH₂C₆H₅ <br> \| <br> COOCH₃ | 91 |
| 73 | B₁ | degluco-teicoplanin | H₂N—CH(CH₂)₄NHCOOCH₂C₆H₅ <br> \| <br> COOCH₃ | 41 |
| 74 | B₃ | teicoplanin A₂ | $$H_2N-CH(CH_2)_3-NHC(=NH)-NH-NO_2$$ <br> \| <br> COOCH₂C₆H₅ | 64 |
| 75 | A₃ | teicoplanin A₂ | HN(CH₃)₂(.HCl) | 90 |
| 76 | A₂ | teicoplanin A₂ | H₂N—CH₂—(1-ethylpyrrolidin-2-yl) 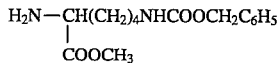 | 67 |
| 77 | A₂ | teicoplanin A₂ | H₂N(CH₂)₃—N(morpholino) 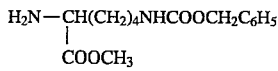 | 82 |
| 78 | B₂ | t-BOC-deglucoteicoplanin | H₂N(CH₂)₃—N(morpholino) 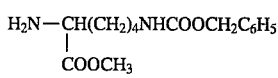 | 49 |
| 79 | B₂ | t-BOC-deglucoteicoplanin | H₂N—CH₂—(1-ethylpyrrolidin-2-yl) 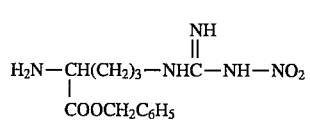 | 53 |
| 80 | A₂ | teicoplanin A₂ | H₂N(CH₂)₆NH₂ | 21 |
| 81 | A₂ | teicoplanin A₂ | H₂N(CH₂)₄N(CH₃)₂ | 71 |
| 82 | A₁ | teicoplanin A₂ | H₂N-(quinuclidinyl) 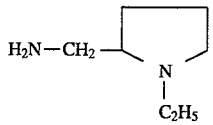 | 84 |
| 83 | B₂ | t-BOC-deglucoteicoplanin | H₂N-(quinuclidinyl) 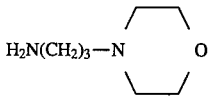 | 63 |
| 84 | E₂ | | Compound 27 | 39 |
| 85 | A₃ | teicoplanin A₂ | H₂NCH₂COOC₂H₅ (HCl) | 83 |
| 86 | F₂ | | Compound 85 | 91 |
| 87 | A₁ | teicoplanin A₂ | H₂N(CH₂)₅N(CH₃)₂ | 66 |
| 88 | A₁ | teicoplanin A₂ | H₂N(CH₂)₇N(CH₃)₂ | 58 |
| 89 | A₂ | Teicoplanin A₂ | H₂N—(piperidyl)—N—CH₂—C₆H₅ 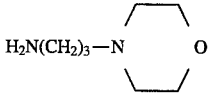 | 61 |
| 90 | A₄ | teicoplanin A₂ | H₂N—(piperidyl)—N—CH₂—C₆H₅ 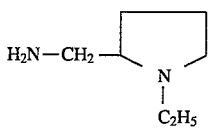 | 37 |
| 91 | A₂ | teicoplanin A₂ | H₂NCH₂—(2-pyridyl) 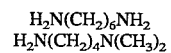 | 26 |

TABLE II-continued

| Compound | Method of preparation | Starting material | | Yield % |
|---|---|---|---|---|
| 92 | $A_3$ | teicoplanin $A_2$ | $H_2N-\underset{\underset{COOCH_3}{\|}}{CH}(CH_2)_3CH_3(.HCl)$ | 74 |
| 93 | $A_2$ | teicoplanin $A_2$ | $\underset{HN-(CH_2)_2N(CH_3)_2}{\overset{CH_3}{\|}}$ | 42 |
| 94 | $B_2$ | t-BOC-degluco-teicoplanin | $H_2N(CH_2)_2N(CH_3)_2$ | 39 |
| 95 | $A_1$ | teicoplanin $A_2$ | $H_2N(CH_2)_2N(CH_3)_2$ | 48 |
| 96 | $A_2$ | teicoplanin $A_2$ | $H_2N(CH_2)_4NH_2$ | 46 |
| 97 | $E_1$ | | Compound 81 | 71 |
| 98 | $A_7$ | t-BOC-degluco-teicoplanin | $H_2N-\underset{\underset{COOCH_2C_6H_5}{\|}}{CH}(CH_2)_3NHC\overset{NH}{\overset{\|}{\|}}NHNO_2$ | 33 |
| 99 | $E_1$ | | Compound 96 | 29 |
| 100 | $E_1$ | | Compound 87 | 61 |
| 101 | $E_1$ | | Compound 88 | 63 |
| 102 | $E_2$ | | Compound 80 | 29 |
| 103 | $E_1$ | | Compound 42 | 64 |
| 104 | $F_2$ | | Compound 105 | 86 |
| 105 | $A_3$ | teicoplanin $A_2$ | $H_2N-\underset{\underset{COOCH_3}{\|}}{CH}(CH_2)_3NHC\overset{NH}{\overset{\|}{\|}}-NHNO_2(.HCl)$ | 85 |

HPLC Analysis

The following table reports the $R_t$ of representative examples of the compounds of the invention. The assays were run with a VARIAN model 5000 LC pump equipped with a 20 µl loop injector. RHEODYNE Model 7125 and a PERKIN-ELMER LC 15 UV detector at 254 nm.

Columns: pre-column (1.9 cm) HIBAR LICHROCART 25-4 MERCK pre-packed with LICHROSORB RP-8 (20–30 µm) followed by a column HIBAR RT 250-4 MERCK pre-packed with LICHROSORB RP-8 (10 µm).

Eluents: A, 0.2% aq. $HCOONH_4$ and B, $CH_3CN$

Injection: 20 µl—Flow rate: 2 ml/min.

The reaction is monitored by injecting, at established times, samples of the solutions (or suspensions) diluted with the solvent mixture ($CH_3CN$: $H_2O$, 6:4 (v/v) enough to obtain final concentrations of either 1, 2 or 3 mg/ml.

Method A: linear step gradient from 5 to 75% of B in A in 35 min according to the following program:

| Time (min) | % B in A |
|---|---|
| 0 | 5 |
| 10 | 23 |
| 20 | 30 |
| 30 | 50 |
| 35 | 75 |

Method B: linear gradient from 5 to 60% of B in A in 30 min.

Method C: linear gradient from 20 to 60% of B in A in 30 min.

Method D: suitable chromatographic conditions to compare all the teicoplanin amides with deglucoteicoplanin. HPLC automatic apparatus: Hewlett-Packard mod. 1084

Column: HIBAR (Merck) LICHROSORB RP-8 (7µm)

Flow rate: 1.5 ml/min.

Eluents: A, 0.02 M aq. $NaH_2PO_4/CH_3CN$ 25/75 (v/v) B, 0.02 M aq. $NaH_2PO_4/CH_3CN$ 95/5 (v/v)

Elution: linear step gradient from 8 to 60% of B in A in 48 min., according to the following program:

| Time (min) | % B in A |
|---|---|
| 0 | 8 |
| 40 | 40 |
| 45 | 60 |
| 48 | 60 |

TABLE III a) HPLC analysis of amides of teicoplanin $A_2$ (formula I wherein A is N[($C_{10}$–$C_{11}$)aliphatic acyl]-β-D-2-deoxy-2-amino-glucopyranosyl, B is N-acetyl-β-D-2-deoxy-2-aminoglucopyranosyl, M is α-D-mannopyranosyl) (Method A)

| | $t_R$ (min) | | | | | |
|---|---|---|---|---|---|---|
| Compound | 1* | 2* | 3* | 4* | 5* | k** |
| 1 | 22.9 | 23.6 | 23.9 | 25.3 | 25.5 | 1.475 |
| 2 | 23.4 | 24.2 | 24.5 | 25.8 | 26.1 | 1.512 |
| 3 | 26.4 | 27.0 | 27.3 | 28.2 | 28.4 | 1.687 |
| 4 | 19.6 | 20.6 | 21.2 | 22.9 | 23.2 | 1.287 |
| 5 | 23.6 | 24.1 | 24.4 | 25.6 | 25.9 | 1.506 |
| 6 | 20.3 | 21.2 | 21.7 | 23.5 | 23.7 | 1.325 |
| 26 | 21.1 | 22.2 | 22.7 | 24.2 | 24.4 | 1.387 |
| 27 | — | 17.3 | 17.6 | 18.8 | 19.0 | 1.081 |
| teicoplanin $A_2$-2 | 15.1 | 16.0 | 16.4 | 18.1 | 18.5 | 1 |

TABLE III-continued b) HPLC analysis of amides of antibiotic L 17054
(formula I wherein A represents hydrogen,
B is N-acetyl-β-D-2-deoxy-2-aminoglucopyranosyl,
M is α-D-mannopyranosyl) (Method B)

| Compound | $t_R$ (min) | K |
|---|---|---|
| 7 | 14.9 | 1.367 |
| 8 | 15.2 | 1.394 |
| 9 | 18.0 | 1.651 |
| 10 | 13.6 | 1.248 |
| 11 | 15.1 | 1.385 |
| 12 | 13.5 | 1.238 |
| 28 | 13.7 | 1.257 |
| 29 | 12.2 | 1.119 |
| antibiotic L 17054 | 10.9 | 1 | c) HPLC analysis of amides of antibiotic L 17046
(formula I wherein A and M represent hydrogen,
B represents N-acetyl-β-D-2-deoxy-aminoglucopyranosyl)
(Method B)

| Compound | $t_R$ (min) | K |
|---|---|---|
| 13 | 16.7 | 1.403 |
| 14 | 15.1 | 1.269 |
| 15 | 17.6 | 1.479 |
| 16 | 17.61 | 1.479 |
| 17 | 14.6 | 1.227 |
| antibiotic L 17046 | 11.9 | 1 | d) HPLC analysis of amides of deglucoteicoplanin
(formula I wherein A, B, and M represent hydrogen atoms)
(Method C)

| Compound | $t_R$ (min) | K |
|---|---|---|
| 18 | 19.2 | 1.524 |
| 19 | 20.3 | 1.611 |
| 20 | 25.2 | 2 |
| 21 | 16.4 | 1.302 |
| 22 | 20.6 | 1.635 |
| 23 | 17.2 | 1.365 |
| 24 | 19.1 | 1.516 |
| 25 | 16.3 | 1.294 |
| 30 | 22.9 | 1.817 |
| 31 | 14.5 | 1.150 |
| deglucoteicoplanin | 12.6 | 1 | e) HPLC analysis according to method D
($K' = t_R/t_R$ of deglucoteicoplanin)

| Compound | K' |
|---|---|
| (deglucoteicoplanin ($t_R$ = 14.78 min.) | 1.00) |
| (teicoplanin $A_2$ | 1.75) |
| 1 | 2.09 |
| 2 | 2.16 |
| 3 | 2.60 |
| 4 | 2.13 |
| 5 | 2.15 |
| 6 | 2.06 |
| 7 | 0.85 |
| 8 | 0.89 |
| 9 | 1.45 |
| 10 | 0.85 |
| 11 | 0.88 |
| 12 | 0.86 |
| 13 | 1.00 |
| 14 | 1.03 |
| 15 | 1.05 |
| 16 | 1.18 |
| 17 | 1.05 |
| 18 | 1.32 |
| 19 | 1.48 |
| 20 | 2.48 |
| 21 | 1.36 |
| 22 | 1.44 |
| 23 | 1.38 |
| 24 | 1.99 |
| 25 | 1.49 |
| 26 | 2.13 |
| 27 | 1.93 |
| 28 | 0.97 |
| 29 | 0.74 |
| 30 | 2.77 |
| 31 | 1.19 |
| 32 | |
| 33 | |
| 71 | 2.14 |
| 73 | 1.44 |
| 74 | 2.60 |
| 75 | 2.03 |
| 82 | 2.08 |
| 83 | 1.36 |
| 85 | 2.03 |
| 86 | 1.78 |
| 89 | 2.88 |
| 90 | 1.90 |
| 91 | 2.11 |
| 92 | 2.14 |
| 104 | 1.79 |
| 105 | 2.10 |

*components of the teicoplanin $A_2$ complex

**k = relative retention time = $\dfrac{t_R \text{ amide}}{t_R \text{ teicoplanin } A_2, \text{ component 2}}$ The K' values for the complex derivatives refer to the component 2

The following table (Table IV) reports the acid-base titration data of some representative compounds of the invention. The assays were carried out in METHYLCELLOSOLVE/H$_2$O, 4:1(v/v). A sample is dissolved in METHYLCELLOSOLVE/H$_2$O, 4:1(v/v) (10 umole in about 20 ml) and then 0.01N HCl (2 ml) is added and the mixture is titrated with 0.01N KOH in the same solvent mixture.

TABLE IV

| | | | Acid base titration | | | | |
|---|---|---|---|---|---|---|---|
| Compound | Formula[1] | Salt form | MW[2] | EW | pK$_1$ | pK$_2$ | pK$_3$[3] |
| 1 | | Acetate | | | | | |
| 2 | | hydrochloride | 1923 | 961.5 | 6.25 | 7.8 | |
| 3 | | " | 2069.6 | 1034.8 | 6.3 | 8.0 | |
| 4 | | Acetate | 1917 | 639 | 5.4 | 7.9 | (6.8) |
| 5 | | " | 2071.8 | 690.6 | 5.9 | 8.5 | (7.1) |
| 6 | | acetate | 2113.5 | 704.5 | 5.3 | 7.8 | (6.6) |
| 7 | $C_{77}H_{80}Cl_2N_{10}O_{27}$ | Di-trifluoroacetate | 2166 | 1083 | 6.4 | 7.9 | |

TABLE IV-continued

| | | Acid base titration | | | | | |
|---|---|---|---|---|---|---|---|
| Compound | Formula[1] | Salt form | MW[2] | EW | $pK_1$ | $pK_2$ | $pK_3$[3] |
| 8 | $C_{79}H_{84}Cl_2N_{10}O_{27}$ | " | | | | | |
| 9 | $C_{83}H_{92}Cl_2N_{10}O_{27}$ | " | | | | | |
| 10 | $C_{78}H_{80}Cl_2N_{10}O_{28}$ | " | 2076 | 1038 | 5.25 | 6.4 | |
| 11 | $C_{78}H_{80}Cl_2N_{10}O_{27}$ | " | 1824 | 912 | 6.5 | 8.3 | |
| 12 | $C_{77}H_{78}Cl_2N_{10}O_{27}$ | " | | | | | |
| 13 | $C_{71}H_{70}Cl_2N_{10}O_{22}$ | Di-hydrochloride | | | | | |
| 14 | $C_{72}H_{70}Cl_2N_{10}O_{23}$ | " | 1632 | 816 | 5.3 | 6.8 | |
| 15 | $C_{72}H_{70}Cl_2N_{10}O_{22}$ | " | 1607.8 | 803.9 | 6.25 | 7.85 | |
| 16 | $C_{70}H_{65}Cl_2N_9O_{24}$ | Hydrochloride | | | | | |
| 17 | $C_{68}H_{61}Cl_2N_9O_{24}$ | hydrochloride | 1682.5 | 1682.5 | 6.4 | | |
| 18 | $C_{63}H_{57}Cl_2N_9O_{17}$ | di-trifluoroacetate | | | | | |
| 19 | $C_{65}H_{61}Cl_2N_9O_{17}$ | hydrochloride | 1260 | 630 | 6.30 | 8.0 | |
| 20 | $C_{69}H_{69}Cl_2N_9O_{17}$ | hydrochloride | 1505.1 | 752.5 | 6.1 | 8.3 | |
| 21 | $C_{64}H_{57}Cl_2N_9O_{18}$ | di-trifluoroacetate | 1426 | 713 | 5.01 | 6.8 | |
| 22 | $C_{64}H_{57}Cl_2N_9O_{17}$ | " | 1640 | 820 | 6.4 | 7.8 | |
| 23 | $C_{63}H_{55}Cl_2N_9O_{17}$ | " | 1742.6 | 871.3 | 5.6 | 6.8 | |
| 24 | $C_{67}H_{56}Cl_2N_{10}O_{17}$ | acetate | 1399 | 466.3 | 5.75 | 7.4 | (6.6) |
| 25 | $C_{62}H_{52}Cl_2N_8O_{18}$ | trifluoroacetate | 1425 | 1425 | 6.6 | | |
| 26 | | free base | 2072 | 2072 | 6.7 | | |
| 27 | | internal salt | 2382.4 | 1191.2 | 6.8 | | |
| 28 | | trifluoroacetate | | | | | |
| 29 | | trifluoroacetate | 2252 | 1126 | 6.75 | | 4.8 |
| 30 | | trifluoroacetate | 1462.4 | 731.2 | 5.4 | 6.9 | |
| 31 | | hydrochloride | 1730 | 1730 | 6.45 | | |
| 32a | | di-hydrochloride | | | 4.8 | 7.0 | 9.4 |
| 32b | | hydrochloride | | | 5.1 | 7.2 | 9.7 |
| 32c | | di-hydrochloride | | | 5.1 | 7.0 | 9.4 |
| 66 | | trifluoroacetate | | | 4.8 | | |
| | | | | | 6.1 | 7.2 | |
| 68 | | hydrochloride | | | | 6.5 | |
| 69 | | internal salt | | | 4.9 | 7.2 | |
| 71 | | di-hydrochloride | | | | 6.5 | 8.9 |
| 73 | | di-hydrochloride | | | | 6.5 | 8.9 |
| 75 | | hydrochloride | | | | 6.6 | |

Notes to Table IV:
[1]The molecular formula for the single components of the complex are as follows:
Teicoplanin $A_2$ component 1: 1877.7 for $C_{88}H_{95}Cl_2N_9O_{33}$
Teicoplanin $A_2$ component 2: 1879.7 for $C_{88}H_{97}Cl_2N_9O_{33}$
Teicoplanin $A_2$ component 3: 1879.7 for $C_{88}H_{97}Cl_2N_9O_{33}$
Teicoplanin $A_2$ component 4: 1893.7 for $C_{89}H_{99}Cl_2N_9O_{33}$
Teicoplanin $A_2$ component 5: 1893.7 for $C_{89}H_{99}Cl_2N_9O_{33}$
[2]The difference between the found and theoretical value are due mainly to the presence of solvents (found value higher than theoretical value) or traces of excess of the acid used for salifying (found value lower than theoretical value).
[3]The values between brackets are due to the titration of the carboxylic function of the salifying acid.

TABLE V

| | IR Data ($cm^{-1}$; nujol) | | | | | | |
|---|---|---|---|---|---|---|---|
| Compound | ν NH glycosidic and phenolic ν OH | ν C=O (amide I) | δ NH (amide II) | glycosidic δ OH, ν C—O | phenolic ν C—O | ν COO⁻ | δ $CF_3$ |
| 1 | 3700-3100 | 1655 | 1510 | 1220-1180 1110-950 | o.b. | 1550 | |
| 2 | 3700-3100 | 1655 | 1510 | 1270-1180 1120-950 | o.b. | | |
| 3 | 3700-3100 | 1655 | 1510 | 1270-1180 1120-950 | o.b. | | |
| 4 | 3700-3100 | 1655 | 1510 | 1250-1180 1120-950 | o.b. | 1550 | |
| 5 | 3700-3100 | 1655 | 1510 | 1270-1180 1120-950 | o.b. | 1550 | |
| 6 | 3700-3100 | 1655 | 1510 | 1270-1190 1120-950 | o.b. | 1550 | |
| 7 | 3700-3100 | 1655 | 1515 | 1270,1190 1110-950 | o.b. | — | 1200,1135 |
| 8 | 3700-3100 | 1655 | 1515 | 1250-1160 | o.b. | — | 1200,1135 |
| 9 | 3700-3100 | 1650 | 1515 | 1270-1180 | o.b. | 1665 | 1200,1140 |

TABLE V-continued

| | IR Data (cm$^{-1}$; nujol) | | | | | | |
|---|---|---|---|---|---|---|---|
| Compound | ν NH glycosidic and phenolic ν OH | ν C=O (amide I) | δ NH (amide II) | glycosidic δ OH, ν C—O | phenolic ν C—O | ν COO$^-$ | δ CF$_3$ |
| 10 | 3700-3100 | 1655 | 1515 | 1100-950 1250-1180 1000-950 | o.b. | — | 1200,1140 |
| 11 | 3700-3100 | 1655 | 1515 | 1270-1180 1100-950 | o.b. | 1665 | 1200,1135 |
| 12 | 3700-3100 | 1655 | 1515 | — | o.b. | 1665 | 1200,1140 |
| 13 | 3700-3100 | 1655 | 1515 | 1230,1150 1100-990 | o.b. | — | — |
| 14 | | | | | | | |
| 15 | 3700-3100 | 1655 | 1515 | 1230,1140 1100-990 | o.b. | — | — |
| 16 | | | | | | | |
| 17 | 3700-3100 | 1655,1735 (ester) | 1515 | 1250,1150 1100-990 | o.b. | | |
| 18 | 3700-3100 | 1655 | 1515 | — | 1230,1200, 1080,1005 | — | 1200 1135 |
| 19 | 3700-3100 | 1650 | 1515 | — | 1230,1200 1080,1005 | — | — |
| 20 | 3700-3100 | 1655 | 1515 | — | 1230,1200 1005 | — | — |
| 21 | 3700-3100 | 1655 | 1515 | — | 1230,1200, 1060,1005 | 1665 | 1200,1135 |
| 22 | 3700-3100 | 1655 | 1515 | — | 1200,1060 1010 | 1665 | 1200,1140 |
| 23 | 3700-3100 | 1655 | 1515 | — | 1230,1200 1060,1005 | 1665 | 1200,1135 |
| 24 | 3700-3100 | 1655 | 1515 | — | 1230,1200 1085,1005 | 1560 | — |
| 25 | 3700-3100 | 1655 | 1515 | — | 1230,1200 1060,1005 | 1660 | 1200,1135 |
| 26 | 3700-3100 | 1650 | 1515 | 1270-1180 1100-950 | o.b. | — | — |
| 27 | 3700-3100 | 1650 | 1510 | 1250-1200 1100-950 | o.b. | — | — |
| 28 | | | | | | | |
| 29 | 3700-3100 | 1655 | 1510 | 1250-1200 1100-950 | o.b. | 1660 | 1200,1135 |
| 30 | 3700-3100 | 1655 | 1515 | — | — | 1670 | 1200,1135 |
| 31 | 3700-3100 | 1650 | 1515 | — | 1230,1080 1010 | — | — |
| 32a | 3700-3100 | 1655 | 1510 | 1250-1190 1110-930 | o.b. | | |
| 32b | 3700-3100 | 1650 | 1510 | 1250-1190 1100-940 | o.b. | | |
| 32c | 3700-3100 | 1655 | 1510 | 1250-1190 1100-940 | o.b. | | |
| 68 | 3700-3100 | 1730 (ester) 1650 (amide I) | 1510 | 1250-1190 1100-940 | o.b. | | |
| 71 | 3700-3100 | 1725 (ester) 1650 (amide I) | 1505 | 1270-1190 1100-940 | o.b. | | |
| 73 | 3700-3100 | 1725 (ester) 1645 (amide I) | 1510 | | o.b. | | |
| 77 | 3700-3100 | 1650 | 1515 | | 1230 1010 | | |
| 78 | 3700-3100 | 1660 | 1515 | | 1230 1010 | | 1200 1135 |

Note:
The ν COO$^-$ and δ CF$_3$ data relate to the salifying acid.
o.b. = Overlapped bands.

TABLE VI

| | UV Data (λmax, nm) | | | | | |
|---|---|---|---|---|---|---|
| | Compounds Nos. 1–23 and 25–31 | compound No. 24 | Compound 32a | Compound 32b and 32c | Compound 66 | Compound 68 |
| Methanol | 280 | 282 | 272 | 276 | | 280 |
| 0.1N HCl | 278 | 280 | 276 | 276 | 279 | 280 |

TABLE VI-continued

| UV Data (λmax, nm) | | | | | | |
|---|---|---|---|---|---|---|
| Phosphate buffer pH 7.4 | 280 | 278 | 276 | 276 | 279 | 280 |
| Phosphate buffer pH 9.0 | 280 | 283 | 270 | 270 | | 280 |
| 0.1N KOH | 298 | 298 | 294 | 294 | 296 | 298 |

| | Compound 69 | Compound 70 | Compound 71 | Compound 72 | Compound 73 | Compound 75 |
|---|---|---|---|---|---|---|
| Methanol | | | | | | |
| 0.1N HCl | 280 | 280 | 279 | 279 | 278 | 280 |
| Phosphate buffer pH 7.4 | 280 | 280 | 280 | 280 | 279 | 280 |
| Phosphate buffer pH 9.0 | 280 | | | | | |
| 0.1N KOH | 296 | 298 | 298 | 298 | 298 | 298 |

| | Compound 76 and 79 | Compounds 77, 78 and 81 | Compounds 80, 85–88, 93, 97, 100, and 101 | Compounds 82 and 83 | Compounds 84, and 92 | Compound 103 |
|---|---|---|---|---|---|---|
| Methanol | | | | 280 | | |
| 0.1N HCl | 280 | 279 | 279 | 278 | 280 | 280 |
| Phosphate buffer pH 7.4 | 280 | 280 | 279 | 279 | 279 | 280 |
| Phosphate buffer pH 9.0 | | | | 280 | | |
| 0.1N KOH | 298 | 298 | 298 | 297 | 298 | 300 |

Table VII reports 1H NMR data obtained at 250 MHz with a BRUKER AM-250 Spectrometer in DMSO-$d_6$ at 20° C. at a sample concentration of 20 mg/ml (internal standard: TMS,=0.00 ppm).

TABLE VII $^1$H-NMR spectra (δ, ppm) in DMSO-$d_6$

| Compound | |
|---|---|
| 1 | 0.83, 1.13–1.17, 1.42, 2.02 (acyl chain); 1.87 (acetylglucosamine), 2.21 (N—CH$_3$); 3.48 (mannose); 5.58 (C$_{27}$H); 5.10 (C$_{26}$—H); 6.33–7.79 (aromatic protons) |
| 2a | 0.85, 1.23, 1.49, 2.08 (acyl chain); 1.93 (acetylglucosamine); 3.13 (alkylamino group); 4.36–5.71 (peptidic CH's); 6.41–7.92 (aromatic protons) |
| 2b | 0.83, 1.13–1.22, 2.00 (acyl chain); 0.96, 2.60 (ethyl groups); 1.88 (acetylglucosamine); 5.56 (C$_{27}$—H); 5.09 (C$_{26}$—H); 5.71–4.10 (peptidic CH's); 6.29–7.90 (aromatic protons) |
| 3 | 0.84, 1.14, 1.42, 2.01 (acyl chain); 1.90 (acetylglucosamine); 1.70 (alkylamine); 5.57 (C$_{27}$—H); 5.09 (C$_{26}$—H) |
| 4 | 0.84, 1.18, 1.43, 2.02 (acyl chain); 2.44, 3.62 (morpholine); 3.49 (mannose); 1.88 (acetylglucosamine); 5.58 (C$_{27}$—H); 5.10 (C$_{26}$—H) |
| 5 | 0.87, 1.18, 1.44, 2.02 (acyl chain); 1.91 (acetylglucosamine); 3.49 (mannose); 5.57 (C$_{27}$—H); 5.10 (C$_{26}$—H) |
| 6 | 0.84, 1.12, 1.38, 2.03 (acyl chain); 1.86 (acetylglucosamine); 3.46 (mannose); 5.56 (C$_{27}$—H); 5.10 (C$_{26}$—H); 6.34–7.89 (aromatic protons) |
| 7 | 1.92 (acetylglucosamine); 2.76 (N—CH$_3$); 5.60 (C$_{27}$—H); 5.10 (C$_{26}$—H); 6.21–7.95 (aromatic protons) |
| 10 | 1.92 (acetylglucosamine); 3.48 (mannose); 5.61 (C$_{27}$—H); 5.10 (C$_{26}$—H); 3.70 (morpholine); 6.23–7.85 (aromatic protons) |
| 11 | 1.89 (acetylglucosamine); 3.03 (N—CH$_2$); 3.48 (mannose); 4.12–5.69 (peptide protons); 6.25–7.89 (aromatic protons) |
| 12 | 1.89 (acetylglucosamine); 3.48 (mannose); 2.80 (N—CH$_3$); 5.60 (C$_{27}$—H); 5.10 (C$_{26}$—H); 6.34–7.93 (aromatic protons) |
| 13 | 1.89 (acetylglucosamine); 2.74 (N—CH$_3$); 5.50 (C$_{27}$—H); 5.11 (C$_{26}$—H); 6.22–7.97 (aromatic protons) |
| 14 | 1.80 (acetylglucosamine); 4.20–5.60 (peptide protons); 6.30–7.80 (aromatic protons) |
| 15 | 1.90 (acetylglucosamine); 5.51 (C$_{27}$—H); 5.11 (C$_{26}$—H); 6.21–7.88 (aromatic protons) |
| 16 | 1.82 (acetylglucosamine); 4.12–5.60 (peptidic protons); 7.92–6.34 (aromatic protons) |
| 17 | 1.82 (acetylglucosamine); 3.70 (COOCH$_3$); 4.16–5.63 (peptidic protons); 7.92–6.33 (aromatic protons) |
| 18 | 1.79 [(CH$_2$)—CH$_2$—(CH$_2$)]; 2.72 (N—CH$_3$); 2.96 (N—CH$_2$); 5.48 (C$_{27}$—H); 5.08 (C$_{26}$—H); 4.18–5.66 (peptidic CH'S); 6.21–7.78 (aromatic CH's) |

TABLE VII-continued $^1$H-NMR spectra ($\delta$, ppm) in DMSO-$d_6$

| Compound | |
|---|---|
| 19 | 2.64 (N—CH$_2$); 5.49 (C$_{27}$—H); 5.10 (C$_{26}$—H); 6.22–7.79 (aromatic protons) |
| 20 | 0.87, 1.26, 1.39, 1.63, 3.16 (alkylamino groups); 1.90 (acetylglucosamine); 5.49 (C$_{27}$—H); 5.09 (C$_{26}$—H); 6.23–7.79 (aromatic CH's) |
| 21 | 3.66 (morpholine); 5.63 (C$_{27}$—H); 5.07 (C$_{26}$—H); 6.25–7.79 (aromatic protons) |
| 22 | 3.59 (N—CH$_2$); 5.49 (C$_{27}$—H); 5.10 (C$_{26}$—H); 6.18–7.87 (aromatic protons); 8.84–10.01 (phenolic OH's) |
| 23 | 2.78 (N—CH$_3$); 5.49 (C$_{27}$—H); 5.07 (C$_{26}$—H); 6.33–7.79 (aromatic protons) |
| 24 | 3.30 (piperazine CH$_2$); 5.50 (C$_{27}$—H); 5.11 (C$_{26}$—H); 6.19–7.81 (aromatic protons) |
| 25 | 3.60 (morpholine); 5.4 (C$_{27}$—H); 5.07 (C$_{26}$—H); 6.22–7.81 (aromatic protons) |
| 26 | 0.84, 1.11–1.17, 1.42, 2.00 (acyl chain); 3.30 (N—CH$_2$); 5.69–4.06 (peptidic protons); 7.78–6.32 (aromatic protons) |
| 27 | 0.84, 1.22, 1.43, 2.02 (acyl chain); 1.99 (acetylglucosamine); 5.7–4.15 (peptidic CH's); 6.29–7.91 (aromatic protons) |
| 28 | 1.88 (acetylglucosamine); 3.48 (mannose); 3.30 (N—CH$_2$); 5.60 (C$_{27}$—H); 5.10 (C$_{26}$—H); 6.35–7.93 (aromatic protons) |
| 29 | 1.77 (lysine CH$_2$); 2.07 (acetylglucosamine); 3.75–5.58 (peptidic and aromatic protons) |
| 30 | 3.65 (N—CH$_2$); 5.43–4.03 (peptidic CH's); 7.81–6.34 (aromatic CH's) |
| 31 | 3.07, 3.67 (CH$_2$ of the substituent), 4.10–5.63 (peptidic protons); 6.22–7.79 (aromatic protons) |
| 32a | 0.83, 1.13–1.22, 2.02 (acyl chain); 1.88 (acetylglucosamine); 3.48 (mannose); 5.60 (C$_{27}$—H); 5.11 (C$_{26}$—H); 6.30–7.90 (aromatic protons) |
| 32b | 0.83, 1.13–1.22, 2.03 (acyl chain); 1.90 (acetylglucosamine); 3.48 (mannose); 5.60 (C$_{27}$—H); 5.10 (C$_{26}$—H); 6.30–7.90 (aromatic protons) |
| 32c | 0.83, 1.13–1.22, 2.03 (acyl chain); 1.88 (acetylglucosamine); 3.49 (mannose); 5.60 (C$_{27}$—H); 5.11 (C$_{26}$—H); 6.30–7.90 (aromatic protons) |
| 33 | 0.83, 1.14, 1.43, 2.02 (acyl chain); 1.89 (acetylglucosamine); 1.62, 1.85, 3.65 (alkylamino groups); 3.66 (methylester); 3.49 (mannose); 5.59 (C$_{27}$—H), 5.11 (C$_{26}$—H); 6.30–7.92 (aromatic protons) |
| 66 | 2.3 (CH$_2$); 4.10–5.64 (peptidic CH's); 5.48 (C$_{27}$—H); 5.06 (C$_{26}$—H); 6.34–7.90 (aromatic protons) |
| 68 | 0.83, 1.13–1.22, 2.03 (acyl chain); 1.87 (acetylglucosamine); 3.50 (mannose); 3.69 [(COO)CH$_3$]; 5.63 (C$_{27}$—H); 5.14 (C$_{26}$—H); 6.30–7.80 (aromatic protons); 7.33 and 5.00 (benzyl moiety) |
| 69 | 0.83, 1.13–1.22, 2.03 (acyl chain); 1.90 (acetylglucosamine); 3.48 (mannose); 5.60 (C$_{27}$—H); 5.10 (C$_{26}$—H); 6.30–7.90 (aromatic protons) |
| 70 | 0.89, 1.17, 1.50, 2.08 (acyl chain); 1.88 (acetylglucosamine); 2.53 (N—CH$_3$); 2.28 (N—(CH$_3$)$_2$); 3.50 (mannose); 5.58 (C$_{27}$—H); 5.10 (C$_{26}$—H); 6.28–7.90 (aromatic protons) |
| 71 | 0.83, 1.09–1.24, 2.03 (acyl chain); 1.93 (acetylglucosamine); 3.70 [(COO)CH$_3$]; 5.63 (C$_{27}$—H); 5.08 (C$_{26}$—H); 6.20–7.90 (aromatic protons) |
| 73 | 1.39, 1.53, 1.75, 2.52, 3.18 (alkylamino groups); 3.68 (methyl ester); 5.56 (C$_{27}$—H); 5.09 (C$_{26}$—H); 6.32–7.90 (aromatic protons) |
| 74 | 0.81, 1.12–1.25, 2.02 (acyl chain); 1.88 (acetylglucosamine); 3.48 (mannose); 5.60 (C$_{27}$—H); 5.11 (C$_{26}$—H); 6.28–7.93 (aromatic protons) |
| 75 | 0.83, 1.13–1.22, 2.03 (acyl chain); 1.87 (acetylglucosamine); 2.90, 2.74 (N(CH$_3$)$_2$); 5.70–4.10 (peptidic CH's); 7.90–6.20 (aromatic protons) |
| 76 | 0.84, 1.04–1.25, 1.43, 2.02 (acyl chain); 1.88 (acetylglucosamine); 1.24, 3.48 (ethyl group); 1.86, 2.95 (pyrrolidine); 3.68 (C$_{12}$—N); 5.58 (C$_{27}$—H); 5.09 (C$_{26}$—H); 6.31–7.88 (aromatic protons) |
| 77 | 0.84, 1.18, 1.39, 2.05 (acyl chain); 1.89 (acetylglucosamine); 2.45, 3.65 (morpholine); 3.48 (mannose); 5.58 (C$_{27}$—H); 5.09 (C$_{26}$—H) |
| 78 | 3.89, 2.92 (morpholine); 3.65, 3.20, 2.21 (alkylamino groups); 4.10–5.63 (peptidic CH's); 6.30–7.92 (aromatic protons) |
| 79 | 1.23, 3.48 (ethyl group); 1.85, 2.95 (pyrrolidine); 3.64 (CH$_2$—N); 4.12–5.62 (peptide protons) |

TABLE VII-continued

$^1$H-NMR spectra ($\delta$, ppm) in DMSO-$d_6$

| Compound | |
|---|---|
| 80 | 0.84, 1.05–1.26, 1.33, 1.99 (acyl chain); 1.88 (acetylglucosamine); 3.70, 3.01, 1.48 (alkylamino groups); 3.49 (mannose); 5.59 ($C_{27}$—H); 5.10 ($C_{26}$—H); 6.29–7.90 (aromatic protons) |
| 81 | 0.85, 1.23, 1.41, 2.05 (acyl chain); 1.90 (acetylglucosamine); 3.02, 1.51 (alkylamino groups), 2.72 (($CH_3)_2$—N); 3.48 (mannose); 6.30–7.92 (aromatic protons) |
| 82 | 0.84, 1.18, 1.38, 2.05 (acyl chain); 1.89 (acetylglucosamine); 1.58, 2.24, 2.72, 3.12 (quinuclidine); 3.48 (mannose); 6.30–7.92 (aromatic protons) |
| 83 | 1.86, 2.24, 2.71, 3.16, 3.51 (quinuclidine); 4.10–5.85 (peptidic CH's); 6.21–7.87 (aromatic protons) |
| 84 | 1.34–1.58, 2.69 (alkylamino groups); 4.07–5.68 (peptidic CH's); 6.21–7.85 (aromatic protons) |
| 85 | 0.84, 1.19, 1.38, 2.05 (acyl chain); 1.88 (acetylglucosamine); 3.48 (mannose); 4.12–5.60 (peptidic protons); 7.92–6.33 (aromatic protons) |
| 86 | 0.83, 2.00 (acyl chain); 1.88 (acetylglucosamine); 3.48 (mannose); 4.10–5.60 (peptidic protons); 7.90–6.34 (aromatic protons) |
| 87 | 0.83, 1.07–1.55, 2.00 (acyl chain); 1.89 (acetylglucosamine); 1.07–1.55, 3.01, 3.21 (alkylamino groups); 2.28 (N($CH_3)_2$); 3.47 (mannose), 5.57 ($C_{27}$—H); 5.07 ($C_{26}$—H); |
| 88 | 0.84, 1.21–1.45, 2.16 (acetylglucosamine); 3.21, 2.98, 1.96, 1.21–1.45 (alkylamino groups); 2.08 (N—($CH_3)_2$); 3.48 (mannose), 6.26–7.88 (aromatic protons) |
| 89 | 0.87, 1.18, 1.35, 2.03 (acyl chain); 1.87 (acetylglucosamine); 2.98, 2.45, 1.38 (piperidine); 7.13 (benzyl); 3.49 (mannose) |
| 90 | 0.87, 1.18, 1.33, 2.03 (acyl chain); 1.86 (acetylglucosamine); 2.97, 1.34 (piperidine); 3.48 (mannose); 6.19–7.89 (aromatic protons) |
| 91 | 0.83, 1.16; 1.36, 2.04 (acyl chain); 1.88 (acetylglucosamine); 2.97 ($CH_2$-pyridine); 3.49 (mannose); 7.12, 7.24 (pyridine) |
| 92 | 0.84, 1.13, 1.35, 2.01 (acyl chain); 1.87 (acetylglucosamine); 1.25, 1.56 (alkylamino groups); 3.89 ($CH_3$-ester); 3.49 (mannose); 5.59 ($C_{27}$—H), 5.09 ($C_{26}$—H); 6.16–7.83 (aromatic protons) |
| 93 | 2.51 (N—$CH_3$); 2.77 (N—($CH_3)_2$); 3.51, 3.02 (alkylamino groups); 5.58 ($C_{27}$—H); 5.08 ($C_{26}$—H); 6.34–7.91 (aromatic protons) |
| 94 | 2.76 (N–($CH_3)_2$); 3.56, 3.02 (alkylamino groups); 4.10–5.62 (peptidic CH's); 6.29–7.91 (aromatic protons) |
| 95 | 0.84, 1.14, 1.43, 2.05 (acyl chain); 1.88 (acetylglucosamine); 2.52 (N—($CH_3)_2$); 3.48 (mannose); 6.32–7.89 (aromatic protons) |
| 96 | 0.85, 1.15, 1.33, 2.03 (acyl chain); 1.87 (acetylglucosamine); 3.05, 1.41 (alkylamino groups); 3.49 (mannose); 6.29–7.90 (aromatic protons) |
| 97 | 3.24, 2.97, 1.51–1.65 (alkylamino groups); 2.69 (N—($CH_3)_2$); 4.10–5.63 (peptidic CH's); 6.20–7.93 (aromatic protons) |
| 98 | 5.59 ($C_{27}$—H); 5.11 ($C_{26}$—H); 6.28–7.94 (aromatic protons) |
| 99 | 1.23–1.43, 1.52, 2.77, 3.13 (alkylamino groups); 4.12–5.53 (peptidic CH's); 6.20–7.91 (aromatic protons) |
| 100 | 1.22, 1.48, 1.61, 2.98 (alkylamino groups); 2.71 (N—($CH_3)_2$); 4.10–5.71 (peptidic CH's); 6.21–7.93 (aromatic protons) |
| 101 | 1.29, 1.46, 1.61, 2.98, 3.18 (alkylamino groups); 2.70 (N—$CH_3$); 4.05–5.73 (peptidic CH's); 6.22–7.93 (aromatic protons) |
| 102 | 1.21–1.53, 2.76, 3.12 (alkylamino groups); 4.11–5.63 (peptidic CH's); 6.20–7.93 (aromatic protons) |
| 103 | 3.98, 3.37, 1.22–1.85, 0.85 (alkylamino and acyl groups); 4.10–5.65 (peptidic CH's); 6.22–7.90 (aromatic protons) |
| 104 | 0.84, 1.16, 1.49, 2.04 (acyl chain); 1.88 (acetylglucosamine); 3.07, 1.79 1.24 (alkylamino groups); 3.49 (mannose); 6.29–7.92 (aromatic protons) |
| 105 | 0.84, 1.17, 1.52, 2.06 (acyl chain); 1.89 (acetylglucosamine); 3.08, 1.78, 1.23 (alkylamino groups); 3.70 ($CH_3$-ester); 3.48 (mannose); 6.30–7.93 (aromatic protons) |

Isoelectric Point (pI)

The isoelectrofocusing (IEF) technique coupled with bioautography detection has been used for the determination of the pI of representative compounds of the invention using the following materials: AMPHOLINE carrier ampholytes (40% w/v) were purchased from LKB Produketer AB, Bromma, Sweden. Acrylamide, N,N'-methylenbisacrylamide (BIS), N,N,N',N'-tetramethylethylenediamine (TEMED) and ammonium persulfate were from Bio Rad Laboratorie, Richmond, Calif., USA. Glycerol and Antibiotic agar N. 1 (Grove and Randall medium N. 1) were from E. Merck Darmstadt FRG. GEL FIX polyester sheets were purchased from Serva Feinbiochemica Heidelberg. Phenolindo (2,6-dichlorophenol) came from BDH Chemicals Ltd. Poole, England.

Isoelectrofocusing

IEF was made on gel slab using a LKB MULITPHOR 2117 cell and a Bio-Rad Power Supply Model 1420A. Slabs of 24.5×11.5 cm and 1 mm thickness were prepared on a sheet of GEL FIX. Polyacrylamide gels with a concentration of 8% T and with a cross-linkage of 4% C (30% T stock solution was prepared by dissolving 28.8 g of acrylamide and 1.2 g of bis-acrylamide in 100 ml distilled water), glycerol, 3.5% v/v, 2% AMPHOLINE, 0.05% ammonium persulphate as catalyst and 0.05% TEMED as accelerator. The carrier ampholite composition for 35 ml gelling solution was as follows:

1) pH 3.5–10: 1.6 ml AMPHOLINE 3.5–10, 0.05 ml Ampholine 4–6, 0.05 ml AMPHOLINE 7–9 and 0.05 ml Ampholine 8–9.5.
2) pH 2.5–6: 0.4 ml AMPHOLINE 2.5–4, 1.1 ml AMPHOLINE 4–6, 0.2 ml AMPHOLINE 3–10.
3) pH 7–10: 0.5 ml AMPHOLINE 7–9, 0.8 ml AMPHOLINE 8–9.5, 0.4 ml AMPHOLINE 9–11.

The electrode solutions, as recommended by LKB for the respective pH range, were:

| pH range | Anode | Cathode |
| --- | --- | --- |
| 3.0–10 | 1M H$_3$PO$_4$ | 1M NaOH |
| 2.5–6 | 1M H$_3$PO$_4$ | 0.5% AMPHOLINE 5–7 |
| 7.0–10 | 0.1% AMPHOLINE 7–9 | 1M NaOH |

Experimental Conditions

The gel was cooled to 4° C. with the aid of a LKB 2209 refrigerated constant temperature circulator. After prefocusing for 30 min. at 5 W, the samples (20 µl containing 0.2 to 2.5 µg of antibiotic) were loaded into the slot at the cathodic side. Electrofocusing was performed using 10 W constant power and was completed after 3–3½ hours with a final potential of 1400 V.

pI Determination

The pH values were determined by dividing a portion of the gel into 1 cm sections, and eluting the individual pieces at room temperature with 1 ml of 10 mM KCl prior to pH readings.

The isoelectric point of each antibiotic was determined by interpolation on a curve obtained by plotting pH values versus the distance from the anode. The results obtained performing at the two separate ranges of pH are presented in Table VIII below.

Microbiological Development

The antibiotics were revealed by bioautography. Polyacrylamide gel was placed on a 3 mm layer of agar medium N. 1 inoculated with 1% of *Bacillus subtilis* ATCC 6633 spore (0.5 OD at 600 nm). After 10 min the gel was removed and the plate was incubated overnight at 37° C. and examined for inhibition zones. The contrast between the area of lysis and that of bacterial growth was enhanced by use of Phenolindo(2,6-dichlorophenol) 1% w/v (oxidation-reduction indicator).

TABLE VIII

| Isoelectric point (pI) determined by IEF technique | |
| --- | --- |
| Compound | pI |
| 1 | 8.9 |
| 2 | 8.8 |
| 3 | 8.7 |
| 4 | 8.0 |
| 5 | 8.8 |
| 6 | 7.9 |
| 7 | 8.9 |
| 8 | 8.8 |
| 9 | 8.7 |
| 10 | 8.0 |
| 11 | 8.8 |
| 12 | 7.9 |
| 13 | 8.9 |
| 14 | 8.0 |
| 15 | 8.8 |
| 16 | 7.8 |
| 17 | 7.8 |
| 18 | 8.9 |
| 19 | 8.7 |
| 20 | 8.7 |
| 21 | 7.9 |
| 22 | 8.8 |
| 23 | 8.0 |
| 25 | 7.8 |
| 26 | 7.8 |
| 27 | 7.8 |
| 28 | 7.8 |
| 29 | 7.9 |
| 31 | 7.9 |
| 34 | 8.7 |
| 35 | 8.6 |
| 36 | 5.8 |
| 37 | 8.5 |
| 38 | 5.8 |
| 39 | 4.2 |
| 40 | 5.6 |
| 43 | 8.7 |
| 44 | 8.7 |
| 45 | 5.7 |
| 46 | 8.6 |
| 47 | 7.8 |
| 48 | 4.1 |
| 51 | 8.5 |
| 56 | 5.8 |
| 57 | 4.2 |
| 62 | 8.6 |
| 63 | 8.4 |
| 64 | 5.7 |
| 65 | 5.8 |
| 66 | 4.2 |
| 67 | 5.6 |
| 68 | 7.8 |
| 69 | 5.8 |
| 71 | 9.0 |
| 74 | 7.8 |
| 75 | 7.8 |
| 77 | 8.1 |
| 78 | 8.1 |
| 81 | 9.0 |
| 82 | 8.9 |
| 83 | 8.9 |
| 84 | 7.8 |
| 85 | 7.7 |
| 86 | 5.8 |
| 87 | 9.1 |
| 89 | 7.7 |
| 92 | 7.8 |
| 100 | 9.0 |
| 101 | 9.1 |
| 104 | 5.8 |
| 105 | 7.8 |

The antibacterial activity of the compounds of the invention can be demonstrated in vitro by means of standard agar-dilution tests. The culture medium ISOSENSITEST BROTH (Oxoid) and the colture medium TODD-HEWITT BROTH (Difco) are used for growing staphylococci and streptococci, respectively. Broth cultures are diluted so that the final inoculum is about $10^4$ colony forming units/ml (CFU/ml). Minimal inhibitory concentration (MIC) is considered as the lowest concentration which shows no visible growth after 18–24 h incubation at 37° C. The results of the antibacterial testing of representative compounds of formula I are summarized in Table IX below:

TABLE IX

| Microorganism | Compound | | | | |
|---|---|---|---|---|---|
| | 1 | 2 | 3 | 4 | 5 |
| | | | MIC (µg/ml) | | |
| S. aureus ATCC 6538 | 0.12 | 0.12 | 0.25 | N.T. | N.T. |
| S. aureus Tour | 0.25 | 0.5 | 0.5 | 0.5 | 0.25 |
| S. epidermidis ATCC 12228 | 0.06 | 0.12 | 0.06 | 0.12 | 0.06 |
| S. pyogenes C 203 | 0.06 | 0.06 | 0.06 | 0.06 | 0.06 |
| S. pneumoniae UC 41 | 0.06 | 0.06 | 0.06 | 0.12 | 0.12 |
| S. faecalis ATCC 7980 | 0.12 | 0.12 | 0.12 | 0.12 | 0.12 |
| E. coli SKF 12140 | >128 | >128 | >128 | >128 | >128 |
| Proteus vulgaris X 19H ATCC 881 | >128 | >128 | >128 | >128 | >128 |
| Pseudomonas aeruginosa ATCC 10145 | 128 | >128 | >128 | >128 | >128 |

| Microorganism | Compound | | | | |
|---|---|---|---|---|---|
| | 6 | 7 | 8 | 9 | 10 |
| | | | MIC (µg/ml) | | |
| S. aureus ATCC 6538 | 0.12 | 0.25 | 0.12 | 0.5 | N.T. |
| S. aureus Tour | 0.25 | 0.5 | 1 | 2 | 1 |
| S. epidermidis ATCC 12228 | 0.12 | 0.12 | 0.06 | 0.06 | 0.008 |
| S. pyogenes C 203 | 0.06 | 0.12 | 0.12 | 0.12 | 0.12 |
| S. pneumoniae UC 41 | 0.12 | 0.5 | 0.5 | 0.5 | 0.5 |
| S. faecalis ATCC 7980 | 0.06 | 1 | 0.5 | 0.5 | 1 |
| E. coli SKF 12140 | >128 | >128 | >128 | >128 | >128 |
| Proteus vulgaris X 19H ATCC 881 | >128 | 128 | >128 | >128 | >128 |
| Pseudomonas aeruginosa ATCC 10145 | >128 | >128 | >128 | >128 | >128 |

| Microorganism | Compound | | | | |
|---|---|---|---|---|---|
| | 11 | 12 | 13 | 14 | 15 |
| | | | MIC (µg/ml) | | |
| S. aureus ATCC 6538 | N.T. | 0.5 | 0.12 | N.T. | N.T. |
| S. aureus Tour | 0.5 | 2 | 0.12 | 0.5 | 0.12 |
| S. epidermidis ATCC 12228 | 0.25 | 0.12 | 0.06 | 0.12 | 0.06 |
| S. pyogenes C 203 | 0.12 | 0.5 | 0.12 | 0.5 | 0.25 |
| S. pneumoniae UC 41 | 00.5 | 1 | 0.25 | 1 | 0.25 |
| S. faecalis ATCC 7080 | 0.5 | 2 | 0.25 | 0.5 | 0.5 |
| E. coli SKF 12140 | >128 | >128 | 64 | >128 | 128 |
| Proteus vulgaris X 19H ATCC 881 | >128 | >128 | >128 | >128 | >128 |
| Pseudomonas aeruginosa ATCC 10145 | >128 | >128 | >128 | >128 | >128 |

| Microorganism | Compound | | | | |
|---|---|---|---|---|---|
| | 16 | 17 | 18 | 19 | 20 |
| | | | MIC (µg/ml) | | |
| S. aureus ATCC 6538 | 0.5 | N.T. | 0.06 | 0.12 | 0.6 |
| S. aureus Tour | 1 | 0.5 | 0.12 | 0.12 | 0.25 |
| S. epidermidis ATCC 12228 | 0.12 | 0.06 | 0.016 | 0.032 | 0.063 |
| S. pyogenes C 203 | 0.25 | 0.25 | 0.06 | 0.06 | 0.06 |
| S. pneumoniae UC 41 | 1 | 2 | 0.12 | 0.12 | 0.12 |
| S. faecalis ATCC 7080 | 1 | 0.5 | 0.12 | 0.12 | 0.25 |
| E. coli SKF 12140 | 128 | >128 | 8 | 8 | 8 |
| Proteus vulgaris X 19H | >128 | >128 | 16 | 32 | 32 |
| Pseudomonas aeruginosa ATCC 10145 | >128 | >128 | 32 | 32 | 64 |

| Microorganism | Compound | | | | |
|---|---|---|---|---|---|
| | 21 | 22 | 23 | 24 | 25 |
| | | | MIC (µg/ml) | | |
| S. aureus ATCC 6538 | 0.06 | N.T | 0.06 | 0.06 | 0.12 |
| S. aureus Tour | 0.12 | 0.12 | 0.12 | 0.12 | 0.12 |
| S. epidermidis ATCC 12228 | 0.016 | 0.016 | 0.032 | 0.063 | 0.016 |

TABLE IX-continued

| | | | | | | |
|---|---|---|---|---|---|---|
| S. pyogenes C 203 | 0.12 | 0.06 | 0.12 | 0.06 | 0.12 | |
| S. pneumoniae UC 41 | 0.12 | 0.12 | 0.12 | 0.06 | 0.12 | |
| S. faecalis ATCC 7080 | 0.12 | 0.12 | 0.12 | 0.12 | 0.12 | |
| E. coli SKF 12140 | 16 | 8 | 16 | 32 | 16 | |
| Proteus vulgaris X 19H | 128 | 64 | 64 | >128 | 64 | |
| Pseudomonas aeruginosa ATCC 10145 | 64 | 64 | 32 | >128 | 64 | |

| | Compound | | | | | | |
|---|---|---|---|---|---|---|---|
| Microorganism | 26 | 27 | 28 | 29 MIC (µg/ml) | 30 | 31 | 33 |
| S. aureus ATCC 6538 | N.T | N.T | N.T | N.T. | N.T. | N.T. | N.T. |
| S. aureus Tour | 1 | 0.5 | 1 | 2 | 4 | 0.5 | 0.12 |
| S. epidermidis ATCC 12228 | 0.25 | 0.25 | 0.12 | 0.25 | 0.12 | 0.063 | 0.012 |
| S. pyogenes C 203 | 0.06 | 0.06 | 0.5 | 0.5 | 1 | 0.12 | 0.06 |
| S. pneumoniae UC 41 | 0.12 | 0.12 | 0.5 | 1 | 2 | 0.25 | 0.06 |
| S. faecalis ATCC 7080 | 0.12 | 0.12 | 2 | 2 | 2 | 0.25 | 0.12 |
| E. coli SKF 12140 | >128 | >128 | >128 | >128 | >128 | 64 | >128 |
| Proteus vulgaris X 19H | >128 | >128 | >128 | >128 | >128 | >128 | >128 |
| Pseudomonas aeruginosa ATCC 10145 | >128 | >128 | >128 | >128 | >128 | >128 | >128 |

| | Compound | | | | | |
|---|---|---|---|---|---|---|
| Microorganism | 60 | 66 | 70 MIC (µg/ml) | 71 | 73 | 74 |
| S. aureus ATCC 6538 | N.T | N.T. | N.T. | N.T. | N.T. | N.T. |
| S. aureus Tour | 0.25 | 0.12 | 0.12 | 0.12 | 0.06 | 4 |
| S. epidermidis ATCC 12228 | 0.06 | 0.012 | 0.06 | 0.12 | 0.06 | 4 |
| S. pyogenes C 203 | 0.12 | 0.12 | 0.06 | 0.06 | 0.12 | 0.06 |
| S. pneumoniae UC 41 | 0.12 | 0.12 | 0.06 | 0.06 | 0.06 | 0.12 |
| S. faecalis ATCC 7080 | 0.25 | 0.5 | 0.12 | 0.12 | 0.12 | 0.25 |
| E. coli SKF 12140 | 32 | >128 | >128 | >128 | 4 | >128 |
| Proteus vulgaris X 19H | 128 | >128 | >128 | >128 | 32 | >128 |
| Pseudomonas aeruginosa ATCC 10145 | 64 | >128 | >128 | >128 | 32 | >128 |

| | Compound | | | | | |
|---|---|---|---|---|---|---|
| Microorganism | 75 | 76 | 77 MIC (µg/ml) | 78 | 79 | 80 |
| S. aureus ATCC 6538 | N.T. | N.T. | N.T. | N.T. | N.T. | N.T. |
| S. aureus Tour | 0.12 | 0.12 | 0.12 | 0.06 | 0.06 | 0.12 |
| S. epidermidis ATCC 12228 | 0.25 | 0.06 | 0.12 | 0.06 | 0.06 | 0.06 |
| S. pyogenes C 203 | 0.06 | 0.06 | 0.06 | 0.06 | 0.06 | 0.06 |
| S. pneumoniae UC 41 | 0.06 | 0.06 | 0.06 | 0.12 | 0.06 | 0.12 |
| S. faecalis ATCC 7080 | 0.12 | 0.12 | 0.12 | 0.12 | 0.12 | 0.12 |
| E. coli SKF 12140 | >128 | >128 | >128 | 8 | 4 | >128 |
| Proteus vulgaris X 19H | >128 | >128 | >128 | 64 | 32 | >128 |
| Pseudomonas aeruginosa ATCC 10145 | >128 | >128 | >128 | 32 | 64 | >128 |

| | Compound | | | | | |
|---|---|---|---|---|---|---|
| Microorganism | 81 | 82 | 83 MIC (µg/ml) | 84 | 85 | 86 |
| S. aureus ATCC 6538 | N.T. | N.T. | N.T. | N.T. | N.T | N.T |
| S. aureus Tour | 0.12 | 0.12 | 0.12 | 0.12 | 0.25 | 0.12 |
| S. epidermidis ATCC 12228 | 0.06 | 0.06 | 0.06 | 0.06 | 0.12 | 0.12 |
| S. pyogenes C 203 | 0.06 | 0.06 | 0.06 | 0.12 | 0.06 | 0.12 |
| S. pneumoniae UC 41 | 0.12 | 0.06 | 0.06 | 0.12 | 0.06 | 0.12 |
| S. faecalis ATCC 7080 | 0.12 | 0.12 | 0.12 | 0.12 | 0.12 | 0.25 |
| E. coli SKF 12140 | >128 | >128 | 8 | 64 | >128 | >128 |
| Proteus vulgaris X 19H | >128 | >128 | 64 | >128 | >128 | >128 |
| Pseudomonas aeruginosa ATCC 10145 | >128 | >128 | 32 | >128 | >128 | >128 |

| | Compound | | | | | |
|---|---|---|---|---|---|---|
| Microorganism | 87 | 88 | 89 MIC (µg/ml) | 90 | 91 | 92 |
| S. aureus ATCC 6538 | N.T. | N.T. | N.T. | N.T. | N.T. | N.T. |
| S. aureus Tour | 0.12 | 0.12 | 0.12 | 0.12 | 0.12 | 0.5 |

TABLE IX-continued

| | | | | | | |
|---|---|---|---|---|---|---|
| S. epidermidis ATCC 12228 | 0.12 | 0.12 | 0.12 | 0.12 | 0.12 | 0.5 |
| S. pyogenes C 203 | 0.6 | 0.6 | 0.6 | 0.6 | 0.6 | 0.6 |
| S. pneumoniae UC 41 | 0.06 | 0.12 | 0.06 | 0.06 | 0.06 | 0.12 |
| S. faecalis ATCC 7080 | 0.12 | 0.12 | 0.12 | 0.12 | 0.12 | 0.12 |
| E. coli SKF 12140 | >128 | >128 | >128 | >128 | >128 | >128 |
| Proteus vulgaris X 19H | >128 | >128 | >128 | >128 | >128 | >128 |
| Pseudomonas aeruginosa ATCC 10145 | >128 | >128 | >128 | >128 | >128 | >128 |

| | Compound | | | | | |
|---|---|---|---|---|---|---|
| | 93 | 94 | 95 | 96 | 97 | 99 |
| Microorganism | | | MIC ($\mu$g/ml) | | | |
| S. aureus ATCC 6538 | N.T. | N.T. | N.T. | N.T. | N.T. | N.T. |
| S. aureus Tour | 0.06 | 0.06 | 0.12 | 0.12 | 0.12 | 0.06 |
| S. epidermidis ATCC 12228 | 0.06 | 0.06 | 0.06 | 0.06 | 0.06 | 0.06 |
| S. pyogenes C 203 | 0.06 | 0.06 | 0.06 | 0.06 | 0.06 | 0.06 |
| S. pneumoniae UC 41 | 0.06 | 0.06 | 0.06 | 0.12 | 0.12 | 0.12 |
| S. faecalis ATCC 7080 | 0.12 | 0.12 | 0.12 | 0.12 | 0.12 | 0.12 |
| E. coli SKF 12140 | 8 | 4 | >128 | >128 | 8 | 8 |
| Proteus vulgaris X 19H | 64 | 32 | >128 | >128 | 32 | 32 |
| Pseudomonas aeruginosa ATCC 10145 | 64 | 16 | 128 | >128 | 32 | 32 |

| | Compound | | | | | |
|---|---|---|---|---|---|---|
| | 100 | 101 | 102 | 103 | 104 | 105 |
| Microorganism | | | MIC ($\mu$g/ml) | | | |
| S. aureus ATCC 6538 | N.T. | N.T. | N.T. | N.T. | N.T. | N.T. |
| S. aureus Tour | 0.06 | 0.06 | 0.06 | 2 | 0.25 | 0.12 |
| S. epidermidis ATCC 12228 | 0.06 | 0.06 | 0.06 | 0.5 | 1 | 0.12 |
| S. pyogenes C 203 | 0.06 | 0.06 | 0.06 | 0.5 | 0.06 | 0.06 |
| S. pneumoniae UC 41 | 0.12 | 0.12 | 0.06 | 0.5 | 0.06 | 0.06 |
| S. faecalis ATCC 7080 | 0.12 | 0.12 | 0.12 | 1 | 0.25 | 0.12 |
| E. coli SKF 12140 | 8 | 16 | 4 | 64 | >128 | >128 |
| Proteus vulgaris X 19H | 128 | 128 | 64 | >128 | >128 | >128 |
| Pseudomonas aeruginosa ATCC 10145 | 64 | 128 | 64 | 128 | >128 | >128 |

The ED$_{50}$ values (mg/Kg) of representative compounds of the invention in in vivo tests in mice experimentally infected with S. pyogenes L 49 according to the procedure described by V. Arioli et al., Journal of Antibiotics 29, 511 (1976) are reported in table X below:

TABLE X

| | ED$_{50}$ (mg/kg) Route of administration | |
|---|---|---|
| Compound | os. | s.c |
| 1 | 70.7 | 0.047 |
| 2 | 89.6 | 0.046 |
| 3 | ~300 | 0.099 |
| 4 | ~300 | 0.08 |
| 5 | 173 | 0.062 |
| 6 | 115 | <0.03 |
| 7 | >300 | 0.81 |
| 8 | >300 | 0.3 |
| 9 | >300 | 0.3 |
| 10 | >300 | 1.6 |
| 11 | >300 | 0.41 |
| 12 | >300 | 0.95 |
| 13 | >300 | 2.2 |
| 14 | N.T. | N.T. |
| 15 | >300 | 2.2 |
| 16 | >300 | 5 |
| 17 | >300 | ~7 |
| 18 | 140 | 0.31 |
| 19 | >300 | 0.18 |
| 20 | >300 | 0.72 |
| 21 | >300 | 2.2 |

TABLE X-continued

| | ED$_{50}$ (mg/kg) Route of administration | |
|---|---|---|
| Compound | os. | s.c |
| 22 | >300 | 1.6 |
| 23 | >300 | 0.95 |
| 24 | >300 | 0.72 |
| 25 | >300 | 1.02 |
| 26 | 220 | 0.08 |
| 27 | 90 | 0.06 |
| 28 | >300 | 1.6 |
| 29 | >300 | 2.2 |
| 30 | >300 | >10 |
| 31 | >300 | 2.9 |
| 33 | | |
| 60 | | |
| 66 | >300 | 5 |
| 70 | 90 | 0.15 |
| 71 | 72 | 0.08 |
| 73 | >300 | 0.81 |
| 74 | >300 | 0.3 |
| 75 | 139 | 0.08 |
| 76 | 140 | 0.1 |
| 77 | >300 | 0.18 |
| 78 | >300 | 1.4 |
| 79 | >300 | 1.25 |
| 80 | 300 | 0.14 |
| 81 | 90 | 0.1 |
| 82 | 173 | 0.07 |
| 83 | >300 | 0.46 |
| 84 | >300 | 1.65 |

TABLE X-continued

| Compound | ED$_{50}$ (mg/kg) Route of administration | |
|---|---|---|
| | os. | s.c |
| 85 | 300 | 0.10 |
| 86 | 300 | 0.23 |
| 87 | 112 | 0.12 |
| 88 | 300 | 0.18 |
| 89 | >300 | 0.08 |
| 90 | 89.6 | 0.08 |
| 91 | 139 | 0.08 |
| 92 | N.T. | N.T. |
| 93 | >300 | 1.25 |
| 94 | >300 | 1.25 |
| 95 | 140 | 0.09 |
| 96 | 90 | 0.07 |
| 97 | >300 | 0.54 |
| 99 | | |
| 100 | | |
| 101 | | |
| 102 | | |
| 103 | N.T. | N.T. |
| 104 | >300 | 0.2 |
| 105 | >300 | 0.13 |

In view of the above reported antimicrobial activity, the compounds of the present invention can effectively be employed as the active ingredient of antimicrobial preparations used in human and veterinary medicine for the prevention and treatment of infectious diseases caused by pathogenic bacteria which are susceptible to said active ingredients. In such treatments, these compounds may be employed as such or in the form of mixtures in any proportion. The compounds of the present invention can be administered orally, topically or parenterally wherein however, the parenteral administration is preferred. Depending on the route of administration, these compounds can be formulated into various dosage forms. Preparations for oral administration may be in the form of capsules, tablets, liquid solutions or suspensions. As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-liquid form. Topical applications may be formulated in hydrophobic or hydrophilic bases as ointments, creams, lotions, paints, or powders. For rectal administration the compounds of the invention are administered in the form of suppositories admixed with conventional vehicles, such as, for example, cocoa butter, wax, spermaceti or polyethyleneglycols and their derivatives. Compositions for injection may take such forms as suspensions, solutions, or emulsions in oily or aqueous vehicles, and may contain formulatory agents such as suspending, stabilizing and/or dispersing agents. Alternatively, the active ingredient may be in powder form for reconstitution at the time of delivery with a suitable vehicle, such as sterile water. The amount of active principle to be administered depends on various factors such as the size and conditions of the subject to be treated, the route and frequency of administration, and the causative agent involved. The compounds of the invention are generally effective at a dosage comprised between about 0.5 and about 30 mg of active ingredient per Kg of body weight, preferably divided in 2 to 4 administrations per day. Particularly desirable compositions are those prepared in the form of dosage units containing from about 20 to about 300 mg per unit. Representative examples of preparation of pharmaceutical compositions are as follows:

A parenteral solution is prepared with 100 mg of compound No 3 dissolved in 2 ml of sterile water for injection. A parenteral solution is prepared with 250 mg of compound No. 19 hydrochloride dissolved in 3 ml of sterile water for injection. A topical ointment is prepared with 200 mg of compound No 19.

3.6 g of polyethylene glycol 4000 U.S.P.
6.2 g of polyethylene glycol 400 U.S.P.

Besides their activity as medicaments, the compounds of the present invention can be used as animal growth promoters. For this purpose, one or more of the compounds of the invention is administered orally in a suitable feed. The exact concentration employed is that which is required to provide for the active agent in a growth promotant effective amount when normal amounts of feed are consumed. The addition of the active compounds of the invention to animal feed is preferably accomplished by preparing an appropriate feed premix containing the active compounds in an effective amount and incorporating the premix into the complete ration. Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and Co., S. Francisco, USA, 1969 or "Livestock Feeds and Feeding", O and B Books, Corvallis, Oreg., USA, 1977) and are incorporated herein by reference.

EXAMPLE 1

(Procedure A$_1$ reaction of unprotected teicoplanin starting material with the selected amine and preparation of the acetate salt of the final compound)

Preparation of Compounds No. 1 to 6, 26, 34, 35, 82, 87, 88 and 95

To a stirred solution of 1 mmol of teicoplanin A$_2$ complex prepared as described in U.S. Pat. No. 4,239,751 and 2 mmol of the selected amine in 20 ml of dimethylformamide (DMF), a solution of 1.1 mmol of diphenylphosphorylazide (DPPA) in 5 ml of DMF is added dropwise in 10 min while cooling to 0°–5° C. The reaction mixture is stirred for about 6 h at 5° C. and overnight at room temperature, afterwards a solution of 0.5 mmol of DPPA in 2.5 ml of DMF is added dropwise at 0°–5° C. Stirring is continued at room temperature for additional 24 h, then 125 ml of ethyl ether is added and the solid which separates is collected, washed with 100 ml of ether and re-dissolved in 100 ml of a mixture water-:acetonitrile, 8:2 (v/v) adjusted at pH 2,5 with 1N HCl. The resulting solution is applied to a chromatographic column, prepared with 250 g of silanized silica gel (0,063–0,2 mm; Merck) pre-equilibrated with a mixture water:acetonitrile 8:2 (v/v). The Column is developed with a linear gradient elution from 20% CH$_3$CN in 0.001N HCl to 80% CH$_3$CN in 0.01N HCl in 20 h at the rate of 250 ml/h. Fractions of 25 ml are collected and monitored by HPLC. Fractions containing the pure compound of the title are pooled and the resulting solution is brought to pH 8,5 with 1N NaOH, and an equal volume (v/v) of water is then added. This mixture is then extracted with butanol (v/v) and the organic layer is separated, washed with water and concentrated under vacuum at 40° C. until most of the water is eliminated. The cloudy butanolic solution is filtered, ethyl acetate (0.5 v/v, i.e. half a volume of solvent per volume of solution) is added and the suspension (or cloudy solution) which forms is extracted with water (0.5 v/v). The organic layer is concentrated to a small volume, ethyl ether is added and the solid which separates is collected, washed with ether, then dried in vacuo at 50° C. overnight, yielding the title compound as the corresponding free base which is then dissolved in methanol (in general 1 g in 50–100 ml). Glacial acetic acid (0.5 ml per gram of the free base) is added and the resulting solution is stirred a few minutes at room temperature. By adding ethyl ether (300–500 ml), a solid separates which is collected, washed with ether (100 ml) and dried overnight at room temperature, yielding the title compounds as the corresponding monoacetate salt.

EXAMPLE 2

(Procedure $A_2$: Reaction of unprotected teicoplanin starting material with the selected amine and preparation of the hydrochloride salt of the final compound)

Preparation of Compounds No. 13, 18, 76, 77, 80, 81, 89 and 91

The reaction between teicoplanin $A_2$ complex and the selected amine is conducted as described in example 1. Once the crude product of the title is precipitated with ethyl ether and separated as a solid, it is suspended in methanol (about 1 g of substance in 100 ml of solvent). Water is added (v/v) and the resulting solution (or suspension) is brought to pH 2,5 with 1N HCl. Then silanized silica gel (0.063–0.2 mm 5 g per gram of crude product—Merck) and n-butanol (200 ml) are added. The resulting suspension is stirred a few minutes at room temperature, afterwards the solvents are completely evaporated and the residue is put at the top of a chromatographic column containing the same kind of silanized silica gel (100 g) equilibrated with the mixture water:acetonitrile, 95:5 (v/v). The column is developed with linear gradient elutions from 5% to 40% (in the case of compound 13) or 15% to 60% (in the case of compound 18) of $CH_3CN$ in 0,001 N HCl, in 20 h at the rate of 100 ml/h. Fractions of 10 ml are collected and assayed by HPLC (method b). Fractions containing the title compound are pooled and concentrated under vacuum at 45° C. and by adding suitable amounts of n-butanol a final water-free butanolic cloudy solution (about 200 ml) is obtained. After adding 1N HCl (0,2 ml) the solution is concentrated to a small volume under vacuum at room temperature (below 25°). Precipitation with ethyl ether, washing with ether and drying in vacuo at 40° C. overnight, yield the title compound (as the corresponding di-hydrochloride).

EXAMPLE 3

(Procedure $A_3$: Reaction of an unprotected teicoplanin starting material with an acid addition salt of the selected amine in the presence of a base)

Preparation of Compound Nos. 16, 38, 75, 82, 92 and 105

A solution of 0,6 ml (2,8 mmol) of DPPA in 2 ml of DMF is added to a stirred solution of 2,8 g (2 mmol) of antibiotic L 17046 and 0,6 g( 4,2 mmol) of glycine ethyl ester, hydrochloride, in 100 ml of DMF at 0°–5° C. After adding 1.1 ml (8 mol) of triethylamine (TEA) the reaction mixture is stirred 2 h at 5° C. and overnight at room temperature. The reaction course is monitored by HPLC (method b). The resulting solution is poured into 500 ml of ethyl ether and the precipitate which forms is collected and re-dissolved in 500 ml of a mixture water:acetonitrile, 7:3 (v/v) while adjusting the pH at 2.3 with 1N HCl. After adding 600 ml of n-butanol and 200 ml of water, the mixture is brought to pH 8.2 with 1N NaOH under vigorous stirring. The organic layer is separated, washed with 400 ml (2×200 ml) of water, then concentrated to a small volume (about 50 ml) at 50° C. under vacuum. By adding ethyl ether (200 ml) a solid (the title compound as the free base) separates which is collected and re-dissolved in 200 ml of methanolic 0.02 M HCl. By adding ethyl ether (500 ml) a precipitate separates which is collected, washed with ether and dried in vacuo at 40° C. overnight, yielding 1.62 g of compound 16 (as the corresponding hydrochloride).

EXAMPLE 4

(Procedure $A_4$: Reaction of an unprotected teicoplanin starting material with a $HNR^1R^2$ amine having a further amino group and/or further carboxyl groups, all of which are protected, and its subsequent deprotection by catalytic hydrogenation)

Preparation of Compounds 36, 37, 39, 71 and 90

The procedure of the first part of Example 1 (procedure $A_1$) is essentially followed. Once the condensation product bearing either the additional amino or the carboxy functions protected is obtained, it is deprotected by catalytic hydrogenation using Palladium on carbon (as described in the second part of the Example 6 below, procedure $B_1$).

EXAMPLE 5

(Procedure A5: reaction of an unprotected teicoplanin starting material with a HNR1$R^2$ amine having a further amino group and/or further carboxyl groups which are protected and its subsequent deprotection in acidic medium)

Preparation of Compounds 48 and 57

The procedure of the first part of Example 1, (procedure $A_1$) is essentially followed. The selected amine is in this case an amine compound bearing further carboxyl functions which are protected by groups removable under anhydrous acid conditions such as glutamic acid di-butyl ester. Once the condensation product bearing the protected carboxy functions is obtained, it is deprotected in an acid medium consisting of anhydrous trifluoroacetic acid (as described in the second part of Example 7 below, procedure $B_2$).

EXAMPLE 6

(Procedure $B_1$: reaction of a N-protected teicoplanin starting material and a selected amine followed by deprotection by catalytic hydrogenation)

Preparation of Compounds 9, 13, 22, 54, 61 and 73 a) Preparation of the N-benzyloxycarbonyl protected starting material (NCBzO-ST)

A solution of 0,45 ml of benzyl chloroformate in 10 ml of dry acetone is added dropwise, while cooling at 0°–3° C., to a stirred solution of 2 mmol of the selected teicoplanin starting material and 0.5 g of NaHCO$_3$ in 150 ml of a mixture acetone:water, 2:1 (v/v). After about 30 min., 500 ml of water is added and the resulting solution is extracted with 500 ml of ethyl ether. The aqueous layer is adjusted to about pH 3.5 with 1N HCl and then is extracted with 500 ml of n-butanol. The organic layer is separated, washed with 400 ml of water (2×200 ml), then concentrated to a small volume at 45° C. under vacuum. On adding ethyl ether a solid separates which is collected, washed with ether and dried at room temperature in vacuo overnight, yielding the N-CBzO derivative of the teicoplanin starting material having a purity (HPLC titre>90%, method c) enough for the next step (yield>80%)

b) Preparation of the N-CBzO derivative of the teicoplanin amide compound

The condensation of the above obtained N-benzoyloxycarbonyl starting material with the selected amine is carried out in DMF (HPLC, method c) in the presence of DPPA under the same reaction conditions as described in example 1. The N-CBzO-teicoplanin amide compound is obtained as a solid which precipitates from the reaction mixture by adding ethyl ether.

c) Preparation of the teicoplanin amide derivative of the title

The above obtained crude N-CBzO-teicoplanin amide (1 g) is dissolved in a mixture (100 ml) of methanol:0.1N hydrochloric acid, 7:3 (v/v) and the resulting solution is hydrogenated at room temperature and pressure in the presence of (0.5 g) 5% Pd/C. The reaction is generally completed within 1 h (HPLC, method c). The reaction mixture is filtered and to the clear filtrates a mixture of silanized silica gel (0,063–0.2 mm; 4 g Merck) and n-butanol (60 ml) is added. The solvents are then evaporated under vacuum at 45° C. and the residue is applied to a chromatographic column containing the same type of silanized silica gel (100 g) prepared in a mixture water:acetonitrile, 95:5 (v/v). The column is developed with a linear-gradient elution from 5% (compound 9), 10% (compound 13) and 20% (compound 22) CH$_3$CN in 0.001 N HCl to 30% 40% and 55% respectively, CH$_3$CN in H$_2$O in 15 h at the rate of 120 ml/h. Fractions of 12 ml each are collected and assayed by HPLC. Fractions containing the pure compounds of the title are pooled and to the resulting solution n-butanol (v/v) and 1N HCl (2 ml) are added. After concentration to a small volume under vacuum at 40° C., the title compounds are obtained (as the corresponding di-hydrochloride) by precipitating with ethyl ether from the butanolic phase, washing and drying overnight in vacuo at 40° C.

EXAMPLE 7

(Procedure B2: reaction of an N-protected teicoplanin starting material with a selected amine followed by deprotective acid hydrolysis)

Preparation of Compounds 11, 14, 18, 19, 20, 21, 23, 24 25, 31, 52, 53 78 79 83 and 94 a) Preparation of the N-tert-butoxycarbonyl protected teicoplanin starting material (N-t-BOC-ST)

A mixture of 4 mmol of the selected teicoplanin starting material 2 ml (14.5 mmol) of TEA and 2 g (~7 mmol) of tert-butyl 2,4,5-trichlorophenylcarbonate in 100 ml of DMF is stirred 24 h at room temperature. On adding ether (900 ml) a solid separates which is collected and re-dissolved in a mixture (1l) water:methanol 7:3. The resulting solution is brought to pH 3.5 with 1N HCl, then extracted with ether (500 ml). The aqueous layer is extracted again with n-butanol (1 l). The butanolic layer is washed with water (2×500 ml) and concentrated to a small volume under vacuum at 35° C. By adding ethyl ether a solid is precipitated which is collected, washed with ether and dried in vacuo at 40° C. overnight, yielding (the yields are always higher than 90%) the N-t-BOC protected teicoplanin starting material pure enough (HPLC titre>90%, method c) for the next step.

b) Preparation of the N-t-BOC derivative of the teicoplanin amide compound

The condensation of the above obtained N-t-BOC protected teicoplanin starting material with the selected amine is carried out in DMF (HPLC, method c) in the presence of DPPA under the same conditions described in the example 1. Like in the case of the N-CBzO-teicoplanin amide (see example 4 b), the crude N-t-BOC-teicoplanin amide obtained from the reaction mixture after precipitation with ethyl ether is pure enough for use in the deprotection step.

c) Preparation of the teicoplanin amide derivative of the title

A solution of 1 mmol of N-t-BOC-teicoplanin amide in 40 ml of 100% trifluoroacetic acid (TFA) is stirred 10–20 min at 5° C., afterwards the solvent is evaporated under vacuum at 25° C. The oily residue is triturated with ether, then collected and re-dissolved in 150 ml of methanol. Silanized silica gel (0.063–0.2 mm 5 g Merck) is added and the solvent is evaporated under vacuum at 40° C. The residue is put at the top of a column containing the same silanized silica gel (150 g) prepared in the mixture water:acetonitrile 95:5 (v/v). Column chromatography is carried out substantially according to the procedure described in example 4 c. More particularly, the column is developed with a linear gradient elution from 5% CH$_3$CN in 0.001N HCl to 30% CH$_3$CN in H$_2$O in the case of compound 9, with a linear gradient elution from 10% CH$_3$CN in 0.001N HCl to 40% CH$_3$CN in H$_2$O in the case of compound 14 and with a linear gradient from 20% CH$_3$CN in 0.001N HCl to 55% CH$_3$CN in water in the case of compound 22. The flow rate is 120 ml/h and the time is 15 h. Fractions of 12 ml are collected, monitored by HPLC and worked up substantially as already described in example 4c. Fractions containing the pure compounds of the title are pooled and to the resulting solution n-butanol (v/v) and 1N HCl (2 ml) are added. After concentration to a small volume under vacuum at 40° C. the title compound is obtained (as the corresponding di-hydrochloride, except for compound no. 25 which is recovered as mono-hydrochloride) by precipitating with ethyl ether from the butanolic phase, washing and drying overnight in vacuo at 40° C.

EXAMPLE 8

Preparation of the trifluoroacetate salts of teicoplanin compound amides 18–25

A teicoplanin compound amide (amides 18–25) is dissolved (1 g in 300 ml) in a mixture water:acetonitrile, 8:2 (v/v). The resulting solution is brought td pH 8.5 with 0.1N NaOH and extracted (v/v) with n-butanol. The organic layer is separated, washed with water (v/v) and concentrated to a small volume. On adding ether, the solid which separates is collected, washed with ether and dried overnight in vacuo at 35° C., yielding the corresponding free base which is re-dissolved in TFA (1 g in 10 ml) and precipitated with ethyl ether (100–200 ml). After collecting the solid by filtration, washing with ether and drying in vacuo 24 h at room temperature, the title compounds are obtained (18-24, di-trifluoroacetates and 25 trifluoroacetate).

EXAMPLE 9

(Procedure C: transformation of an amide derivative of teicoplanin $A_2$ complex or teicoplanin $A_2$ single components 1, 2, 3, 4 or 5 into the corresponding amide derivative of antibiotic L 17054)

Preparation of Compounds 7 to 12, 28, 29 and 41 to 49

A solution of 1 mmol of the selected amide of teicoplanin $A_2$ complex or of a single component thereof in 200 ml of 90% aqueous TFA is stirred at room temperature for 2 h (HPLC, method a or b). On adding 800 ml of ethyl ether a solid separates which is rapidly collected, washed with ether and dried in vacuo at 40° C. overnight, yielding the title compound (as the corresponding di-trifluoroacetate).

EXAMPLE 10

(Procedure $D_1$: transformation of an amide derivative of teicoplanin $A_2$ complex, of a single component thereof or of antibiotic L 17054 into the corresponding amide derivative of antibiotic L 17046)

Alternative Preparation of Compounds 13 to 15 and 50

A solution of 1 mmol of the proper amide of T-A2-complex or single component thereof or a amide of antibiotic L 17054 in 50 ml of a mixture tetrahydrofuran (THF) or dimethoxyethane (DME):conc. sulfuric acid ($H_2SO_4$), 80:20 (v/v) is stirred 12–48 h at room temperature (HPLC, method b). On adding 250 ml of ethyl ether a solid separates which is collected and re-dissolved in 300 ml of a mixture water-:acetonitrile, 80:20 (v/v). The resulting solution is adjusted to about pH 8.4 with 0.1N NaOH and extracted with 300 ml of n-butanol. The organic layer is separated, washed with 300 ml (2×150 ml) of water and concentrated under vacuum at 40° C. to a small volume after adding 3 ml of 1N HCl. On adding ether a solid separates which is collected, washed with ether and dried overnight in vacuo at room temperature, yielding the title compound (as di-hydrochloride).

EXAMPLE 11

(Procedure $D_2$: transformation of an amide derivative of teicoplanin $A_2$ complex, of a single component thereof or of antibiotic L 17054 into the corresponding amide derivative of antibiotic L 17046)

Alternative Preparation of Compounds 13–15 and 21

A suspension of 1 mmol of the selected amide of teicoplanin $A_2$ complex or a single component thereof or an amide of antibiotic L 17054 in 100 ml of butanol 0.4M (dry) HCl is stirred at 60° C. for 4–6 h (HPLC, method b), then 200 ml of water and 100 ml of n-butanol are added under vigorous stirring at 10° C. while adjusting the pH above at 8.4 with solid $NaHCO_3$. The organic layer is separated, washed with 200 ml (2×100 ml) of water and 3 ml of 1N HCl is added thereto. The resulting butanolic solution is concentrated to a small volume. On adding ethyl ether a solid separates which is collected, washed with ether and dried overnight in vacuo at room temperature, yielding the compound of the title (as the corresponding di-hydrochloride).

For conveniently preparing compound 21 a slight modification of the above procedure is required which is:

the hydrolysis is conducted in butanolic 0.45M HCl at about 65° C. for 16 h, with stirring. The corresponding di-trifluoroacetate is isolated by substituting TFA for HCl in the treatment of the final butanolic solution as reported above.

EXAMPLE 12

(Procedure $E_1$: transformation of an amide derivative of a teicoplanin compound selected from teicoplanin $A_2$ complex, a single component thereof, antibiotic L 17054 and antibiotic L 17046 into the corresponding amide of deglucoteicoplanin)

Preparation of Compounds 18–20, 22, 23, 97, 99, 100, 101 and 103

A suspension of 1 mmol of the selected amide of teicoplanin $A_2$ complex, of antibiotic L 17054, or (13 and 15) of antibiotic L 17046 in 100 ml of 2–3M (dry) HCl in n-butanol is stirred 6–8 h at about 75° C. (HPLC, method b). Then, the solvent is evaporated under vacuum at 45° C., the residue is dissolved in 500 ml of a mixture water:methanol, 80:20 (v/v) and the resulting solution is adjusted to pH 8.5 with 1N NaOH and extracted with 700 ml of a mixture n-butanol-:ethyl acetate, 7:3 (v/v). The organic layer is suspended, washed with 500 ml of water (2×250 ml), 2 ml of TFA is added thereto and then the resulting mixture is concentrated to a small volume under vacuum. On adding ethyl ether a solid separates which is collected, washed with ether and dried in vacuo at 60° C. overnight, yielding the compound of the title (as the di-trifluoroacetate). When necessary, further purification of these compounds may be obtained e.g. by column chromatography according to the procedure described in example 6c.

EXAMPLE 13

(Procedure $E_2$: transformation of an amide derivative of a teicoplanin compound selected from a teicoplanin $A_2$ complex, a single component thereof, antibiotic L 17054 and antibiotic L 17046 into the corresponding amide of deglucoteicoplanin)

Preparation of Compounds 18–20, 22, 23, 30, 84 and 102

A suspension of 1 mmol of the selected amide of teicoplanin $A_2$ complex, or of antibiotic L 17054 or of antibiotic L 17046 in 50 ml of absolute trifluoroethanol (TFE) is stirred at 75° C. for 12–16 h while bubbling dry HCl, then cooled to 10° C. and left overnight at such a temperature. After adding 20 ml of ethyl ether, the crude compound of the title is recovered from the reaction mixture as dark yellow powder. Purification by column chromatography as reported in example 6c yields the pure compound.

EXAMPLE 14

(Procedure $F_1$: transesterification and ester function hydrolysis of a compound of formula I)

Preparation of Compound 17

In a vessel protected with a soda-lime valve, a solution of 3 ml of methanolic 1M KOH (85% commercial pellets) is added dropwise at room temperature to a stirred solution of 1.05 g (~0.7 mmol) of compound 16 (hydrochloride) in 60 ml of methanol. After 1 h, additional 0.75 ml of 1M KOH in methanol is added and stirring is continued for 30 min (HPLC, method b). Then the reaction mixture is cooled to about 5° C. and 3.75 ml of 1N HCl is added. The resulting solution is diluted with 200 ml of $H_2O$ and 100 ml of $CH_3CN$. Silanized silica gel (0.063–0.2 mm, 5 g; Merck) and n-butanol (400 ml) are then added and the solvents are evaporated under vacuum at 40° C. The residue is put at the top of a column containing 200 g of the same silanized silica gel prepared in $H_2O$. The column is developed with a linear gradient from 1 to 60% $CH_3CN$ in $H_2O$ in 20 h at the rate of 250 ml/h and then with a linear gradient from 60% $CH_3CN$ in $H_2O$ to 70% $CH_3CN$ in 0.01N HCl in 60 h at the rate of 150 ml/h. Fractions of 25 ml each are collected, assayed by HPLC and the compound 17 containing fractions (241–254) are pooled. 200 ml of n-butanol is added to the resulting solution which is then concentrated to a small volume under vacuum at 45° C. to give a butanolic suspension. On adding ethyl ether a solid separates which is collected, washed with ether and dried in vacuo at 30° C. overnight, yielding 0.795 g (~78%) of pure compound 17.

By essentially following this procedure, but using larger amounts of methanolic KOH and/or prolonging the reaction time as necessary, the corresponding compound having a free carboxy function instead of the methoxycarbonyl function may be obtained.

EXAMPLE 15

(Procedure $B_3$: reaction of an unprotected or $N^{15}$-protected teicoplanin starting material with a $NHR^1R^2$ amine having a further amino group and/or further carboxy groups, all of which are protected)

Preparation of compounds 68 and 72

A solution of 3 ml (about 14 mmol) of DPPA in 25 ml of DMF is added dropwise to a stirred solution of 12 mmole of teicoplanin $A_2$ complex (in the case of the preparation of compound 68) or $N^{15}$-CBzO-deglucoteicoplanin (in the case of the preparation of compound 72), 13 mmole of $N^\epsilon$-CBzO-Lysine methyl ester, hydrochloride and 24 mmol of triethylamine (TEA) in 225 ml of DMF, in 10 min while maintaining the temperature at 0°–5° C. After stirring 4 h at 0°–5° C. and 24 h at 20° C., the reaction mixture is poured into 1.5 l of ethyl ether and the precipitate which forms is collected by filtration and re-dissolved in 500 ml of a mixture methanol:water, 4:1 (v/v). The resulting solution is cooled to 10° C. and 800 ml of n-butanol is added thereto under stirring. After adjusting the pH at about 8.3 (with 1N NaOH), the organic layer is separated, Washed with 800 ml (2×400 ml) of water, then concentrated to a small volume (about 100 ml) under reduced pressure at 40° C. By adding ethyl ether (400 ml), a solid separates which is collected and dried in vacuo at 40° C. overnight, yielding the title compound.

By essentially repeating the same procedure but starting from teicoplanin $A_2$ component 1, 2, 3, 4, or 5 the corresponding derivative of the single pure components is obtained.

EXAMPLE 16

(Procedure $F_2$: ester function hydrolysis of a compound of formula I)

Preparation of Compounds 64, 69, 86 and 104

A solution of 5 g of $K_2CO_3$ in 500 ml of $H_2O$ is added under stirring at room temperature to a solution of 4 mmol of compound 63 (for preparing compound 64), 68 (for preparing compound 69) 85 (for preparing compound 86) and 105 (for preparing compound 104), in 500 ml of a mixture methanol:water, 1:1 (v/v). After adding 750 ml of n-butanol, the resulting mixture is vigorously stirred for 36 h. The organic layer is separated, the aqueous phase is brought to pH 3.5 with 1N HCl and then extracted with 500 ml of n-butanol. The butanolic solutions are combined, washed with 600 ml of $H_2O$ (2×300 ml) and concentrated to a small volume (50 ml) under vacuum at 40° C. By adding ethyl ether (350 ml) a solid separates which is collected and dried in vacuo at room temperature overnight, yielding the title compound.

EXAMPLE 17

(Procedure $F_3$: esterification of a compound of formula I wherein the group $—NR^1R^2$ contains carboxylic functions)

Preparation of Compound 51

A stirred suspension of 4.1 g (~2 mmol) of compound 27 in 200 ml of 2.5M HCl is absolute ethanol in refluxed for 5 h. The reaction mixture is then concentrated to a small volume (~40 ml) at 50° C. under vacuum. By adding ethyl ether (~260 ml) a solid separates which is collected by filtration and re-dissolved in 50 ml of a mixture acetonitrile:water, 1:1 (v/v). After adding 150 ml of $H_2O$, the resulting solution is loaded on a column of 400 g of silanized silica-gel (Merck) in $H_2O$. The column is developed with a linear gradient from 20 to 70% of $CH_3CN$ in 0.001N HCl in 20 h at the rate of 200 ml/h, while collecting 20 ml of fractions and assaying them by HPLC. Those fractions which contain the pure title compound are combined and the resulting solution is brought to pH 8.0 with 2% $NaHCO_3$. After extraction with n-butanol (v/v), 1N HCl (2.5 ml 1N HCl per 100 ml of the butanolic solution) is added and the resulting organic solution is concentrated to a small volume thus obtaining a dry butanolic suspension that by adding ethyl ether (v/v) gives a solid which is collected by filtration and dried in vacuo at 40° C. overnight, yielding 0.97 g of pure compound 51, as the di-hydrochloride.

EXAMPLE 18

(Procedure G: separation of the amides of teicoplanin $A_2$ complex into their components by reverse-phase column chromatography)

Preparation of Compounds 2b, 32b, 32c, and 71

A solution of 5 mmol of the starting amide derivative of teicoplanin $A_2$ complex in 250 ml of a mixture acetonitrile:water, 1:1 (v/v) is adjusted to pH 3.5 with 1N HCl, afterwards most of the organic solvent is evaporated under vacuum at 20° C. to obtain a slightly cloudy solution which is loaded on a column of 1 kg of silanized silica-gel (Merck) in H$_2$O. The column is developed with a linear gradient from 20% of CH$_3$CN in H$_2$O to 60% of CH$_3$CN in 0.001N N HCl in 20 h at the rate of 200 ml/h, while collecting 20 ml fractions which are monitored by HPLC. Those fractions which contain the amide of teicoplanin A$_2$ component 2 are pooled. Conveniently, also the fractions containing the amides of components 1–3 and 4 and 5 are pooled, respectively. Each solution is then concentrated to a small volume after adding suitable amounts of n-butanol to obtain a dry butanolic suspension from which the compounds of the title, as the free bases, precipitate as usual with ethyl ether. The addition of a small excess of 1N HCl or trifluoroacetic acid before concentration gives the corresponding hydrochlorides or trifluoroacetates, respectively.

EXAMPLE 19

(Procedure A$_6$: reaction of an unprotected teicoplanin starting material with the α-amino group of Nω-nitro-arginine, methyl ester hydrochloride, followed by the cleavage of the protective nitro group of the resulting compound)

Preparation of Compound 33

The first part of the reaction, starting from 16 g (~8 mmol) of teicoplanin A$_2$ and 12 mmol of Nω-nitro-arginine, methyl ester hydrochloride, is carried out according to the procedure A$_3$ described in Example 3, yielding 14 g of compound 105. A solution of 14 g (~6.5 mmol) of this compound in 200 ml of 90% aqueous acetic acid is treated with 3.6 g (~55 g atom) of zinc powder under vigourous stirring at room temperature. The resulting suspension is stirred 30 min. at room temperature, then is it filtered. By adding ethyl acetate (~800 ml) to the filtrate, a powder (~13 g) separates which is collected by filtration and purified by reverse-phase column chromatography on 700 g of silanized silica-gel according to the procedure described in Example 1, yielding 10.2 g of the title compound, as the free base (the yield of this reaction from compound 105 is about 75%).

EXAMPLE 20

(Procedure A$_7$: reaction of a N$^{15}$-protected or unprotected teicoplanin starting material with the α-aminogroup of Nω-nitro-arginine, methyl ester or benzyl ester respectively, followed by subsequent deprotection of the N$^{15}$-t-BOC, or N$^{15}$-CBzO and benzyl protecting groups in acid medium according to procedure A$_5$, or by catalytic hydrogenation, according to procedure A$_4$, respectively, and final displacement of the nitro-group according to procedure A$_6$)

Preparation of Compounds 32a, 59, 60 and 98

The first step, starting from teicoplanin A$_2$ (complex or a single component thereof), N$^{15}$-t-BOC deglucoteicoplanin or N$^{15}$-CBzO deglucoteicoplanin and the proper Nω-nitroarginine derivative, yields the respective protected compounds of the title. By treatment with 100% trifluoroacetic acid the N$^{15}$-t-BOC protecting group is removed and by catalytic hydrogenation over 5–10% Pd/C also the N$^{15}$-CBzO and benzyl groups are displaced. The Nω-nitro derivatives of compounds 32a, 59, 60 and 98 are thus obtained. The Nω-nitro group is subsequently removed following procedure A$_6$, as described in Example 19, yielding the compounds of the title.

We claim:
1. An amide teicoplanin derivative of the formula:

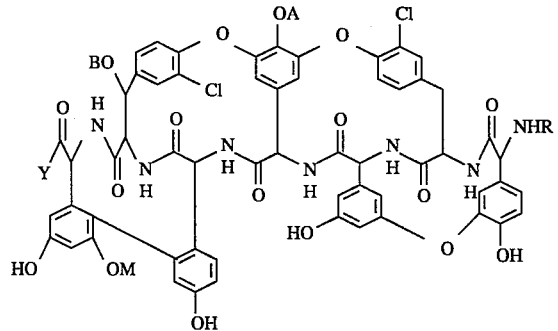

wherein
R represents hydrogen;
Y represents —NH(CH$_2$)$_3$ N(CH$_3$)$_2$;
A represents N-{(C$_{10}$–C$_{11}$)aliphatic acyl}-beta-D-2-deoxy-2-amino-glucopyranosyl;
B represents N-acetyl-beta-D-2-deoxy-2-amino-glucopyranosyl; and
M represents alpha-D-mannopyranosyl,
or an addition salt thereof.

2. An antibacterial pharmaceutical composition comprising an effective amount of a compound of claim 1 in admixture with a pharmaceutically acceptable carrier.

3. A method for treating a bacterial infection in a patient in need thereof which comprises administering to the patient an antibacterially effective amount of a compound of claim 1.

* * * * *